US011351251B2

(12) United States Patent
Li et al.

(10) Patent No.: US 11,351,251 B2
(45) Date of Patent: Jun. 7, 2022

(54) ANTI-PD-L1-ANTI-TIM-3 BISPECIFIC ANTIBODIES

(71) Applicants: Eli Lilly and Company, Indianapolis, IN (US); Zymeworks Inc., Vancouver (CA)

(72) Inventors: Yiwen Li, Woodcliff, NJ (US); Dale Lincoln Ludwig, Rockaway, NJ (US); Yang Shen, Scarsdale, NY (US); Yi Zhang, Edison, NJ (US); Igor Edmondo Paolo D'Angelo, Anmore (CA)

(73) Assignees: Eli Lilly and Company, Indianapolis, IN (US); Zymeworks Inc., Vancouver (CA)

( * ) Notice: Subject to any disclaimer, the term of this patent is extended or adjusted under 35 U.S.C. 154(b) by 542 days.

(21) Appl. No.: 16/299,398

(22) Filed: Mar. 12, 2019

(65) Prior Publication Data
US 2019/0247497 A1    Aug. 15, 2019

Related U.S. Application Data

(63) Continuation of application No. 15/945,011, filed on Apr. 4, 2018, now Pat. No. 10,279,034.

(60) Provisional application No. 62/484,025, filed on Apr. 11, 2017.

(51) Int. Cl.
| | |
|---|---|
| *A61K 39/395* | (2006.01) |
| *A61K 45/06* | (2006.01) |
| *C07K 16/12* | (2006.01) |
| *C07K 16/26* | (2006.01) |
| *C07K 16/28* | (2006.01) |
| *C07K 16/36* | (2006.01) |
| *C07K 16/46* | (2006.01) |
| *A61P 35/00* | (2006.01) |
| *C12P 21/00* | (2006.01) |
| *A61K 9/00* | (2006.01) |
| *A61K 39/40* | (2006.01) |
| *A61K 33/243* | (2019.01) |
| *A61K 31/351* | (2006.01) |
| *A61K 39/00* | (2006.01) |
| *A61K 31/4164* | (2006.01) |

(52) U.S. Cl.
CPC ........ *A61K 39/3955* (2013.01); *A61K 9/0019* (2013.01); *A61K 33/243* (2019.01); *A61K 39/40* (2013.01); *A61K 45/06* (2013.01); *A61P 35/00* (2018.01); *C07K 16/1278* (2013.01); *C07K 16/1282* (2013.01); *C07K 16/26* (2013.01); *C07K 16/283* (2013.01); *C07K 16/2803* (2013.01); *C07K 16/2809* (2013.01); *C07K 16/2827* (2013.01); *C07K 16/2866* (2013.01); *C07K 16/2896* (2013.01); *C07K 16/36* (2013.01); *C07K 16/468* (2013.01); *C12P 21/005* (2013.01); *A61K 31/351* (2013.01); *A61K 31/4164* (2013.01); *A61K 2039/505* (2013.01); *A61K 2039/507* (2013.01); *A61K 2300/00* (2013.01); *C07K 2317/31* (2013.01); *C07K 2317/55* (2013.01); *C07K 2317/64* (2013.01); *C07K 2317/71* (2013.01); *C07K 2317/73* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 9,248,181 B2 | 2/2016 | De Kruif et al. |
| 2017/0058033 A1 | 3/2017 | Ludwig et al. |

FOREIGN PATENT DOCUMENTS

| WO | 2011120134 A1 | 10/2011 |
| WO | 2012037659 A1 | 3/2012 |
| WO | 2012040833 A1 | 4/2012 |
| WO | 2012058768 A1 | 5/2012 |
| WO | 2012116453 A1 | 9/2012 |
| WO | 2013016594 A2 | 1/2013 |
| WO | 2013063702 A1 | 5/2013 |
| WO | 2013166604 A1 | 11/2013 |
| WO | 2014012082 A2 | 1/2014 |
| WO | 2014012085 A2 | 1/2014 |
| WO | 2014018572 A2 | 1/2014 |
| WO | 2014055784 A1 | 4/2014 |
| WO | 2014055897 | 4/2014 |
| WO | 2014067011 A1 | 5/2014 |
| WO | 2014082179 A1 | 6/2014 |
| WO | 2015048312 A1 | 4/2015 |
| WO | 2015181805 A1 | 5/2015 |
| WO | 2015109131 A2 | 7/2015 |
| WO | 2016061142 | 4/2016 |
| WO | 2017034916 | 3/2017 |
| WO | 2017055404 A1 | 4/2017 |
| WO | 2018039020 A1 | 3/2018 |

OTHER PUBLICATIONS

Neugut et al (CCC, 18(2):133-140, 2019, abstract only).*
Sakuishi, Kaori, et al., "Targeting Tim-3 and PD-1 pathways to reverse T cell exhaustion and restore anti-tumor immunity", Journal of Experimental Medicine, 2010, vol. 207.
Spreter Von Kreudenstein T., et al., "Protein engineering and the use of molecular modeling and simulation: The case of heterodimeric Fc engineering", Methods, 2014, 65(1).
Woods, RJ et al., "LC-MS characterization and purity assessment of a prototype bispecific antibody", mAbs, (2013), 5(5).

(Continued)

*Primary Examiner* — Brad Duffy
(74) *Attorney, Agent, or Firm* — Grant Reed

(57) ABSTRACT

The present invention relates to antibodies that are heterodimeric and bind human PD-L1 and human TIM-3, and may be useful for treating cancer alone and in combination with chemotherapy and other cancer therapeutics.

7 Claims, No Drawings
Specification includes a Sequence Listing.

(56) References Cited

OTHER PUBLICATIONS

Von Kreudenstein, Thomas, "Improving biophysical properties of a bispecific antibody scaffold to aid developability", mAbs, 2013, 5(5).
Sasikumar, Pottayil, et al., "Abstract 4861: Oral immune checkpoint antagonists targeting PD-L1/VISTA or PD-L1/Tim3 for cancer therapy" (2016) 76(14 Suppl).
PCT Application No. PCT/US2017/64207 filed Dec. 1, 2017 by Eli Lilly and Company.
International Search Report for International Application No. PCT/US2018/026060.

* cited by examiner

ANTI-PD-L1-ANTI-TIM-3 BISPECIFIC ANTIBODIES

The present invention relates to the field of medicine. More particularly, the present invention relates to bispecific antibodies that bind human programmed cell death 1 ligand 1 (PD-L1) and T-cell immunoglobulin- and mucin-domain-containing protein-3 (TIM-3), and may be useful for treating solid and hematological tumors alone and in combination with chemotherapy and other cancer therapeutics.

Tumor cells escape detection and elimination by the immune system through multiple mechanisms. Immune checkpoint pathways are used in maintenance of self-tolerance and control of T cell activation, but cancer cells can use the pathways to suppress the anti-tumor response and prevent their destruction.

The PD-L1/human programmed cell death 1 (PD-1) pathway is one such immune checkpoint. Human PD-1 is found on T cells and PD-L1 is aberrantly expressed by a variety of tumor types; binding of PD-L1 to PD-1 inhibits T cell proliferation and cytokine production. The PD-1/PD-L1 inhibitory axis has been subjugated by tumors as part of the natural selective process that shapes tumor evolution in the context of an anti-tumor immune response.

TIM-3 is a checkpoint receptor identified to play a key role in the functional suppression of exhausted T-cells. T cells recognizing tumor antigens can be isolated from patients and mouse models, but such cells can exhibit an exhausted phenotype characterized by impairment in cytotoxic functions, effector cytokine production, and proliferation. These T cells can express high levels of the checkpoint regulator TIM-3.

While therapeutic targeting of the PD-1/PD-L1 pathway is clinically validated, there is a variable objective response in cancer patients of between 9-45% in PD-L1-negative and PD-L2-high-positive tumors, and many patients do not achieve durable response. Combined blockade of two or more checkpoint receptors may increase the frequency of objective responses and achieve efficacy in cancer patients who may be refractory to monotherapy with a PD-1 or PD-L1 blocking antibody.

In vitro treatment of tumor infiltrating lymphocytes harvested from CT26 tumor bearing mice with two antibodies, an anti-mouse TIM-3 antibody that can interact with T cells and an anti-mouse PD-L1 antibody that can separately interact with the mouse tumor cells, resulted in more effective control of mouse tumor growth than targeting either pathway alone (Sakuishi et. al. JEM 2010, 207: 2187 and WO 2015/048312).

An oral, small molecule that antagonizes PD-L1 and TIM-3 has been reported (Sasikumar et al., AACR; Cancer Res 2016; 76(14 Suppl):Abstract 4861). This small molecule compound was reported to demonstrate efficacy in syngenic mouse tumor models.

There remains a need to provide compounds that can bind and inhibit both human PD-L1 and human TIM-3, but also have the target specificity and pharmacokinetics of an antibody. In particular, there remains a need to provide heterodimeric bispecific antibodies that bind both human PD-L1 and human TIM-3 where the heterodimeric bispecific antibody enables pairing of two different heavy chains and two different light chains into a single IgG-like antibody. Further, there is a need for the bispecific antibody to resemble native antibody structure as measured by modeling, mass spectrometry, and stability analyses for purposes such as low immunogenicity, stable in vivo pharmacokinetics, and adequate stability. Additionally, there remains a need to provide anti-human PD-L1 and anti-human TIM-3 bispecific antibodies that possess one or more of the following features: simultaneously bind and bridge PD-L1 expressing tumor cells and TIM-3 expressing T-cells, suppress PD-1 and TIM-3 checkpoint inhibitor pathways, exhibit better anti-tumor activity as measured in a tumor model than a combination of an anti-PD-L1 antibody and an anti-TIM-3 antibody, and lack antibody immune effector functions.

Accordingly, the present invention provides an antibody that binds human PD-L1 (SEQ ID NO: 1) and human TIM-3 (SEQ ID NO: 2) comprising:
  a) a first heavy chain (HC) comprising a heavy chain variable region (HCVR) having the amino acid sequence of SEQ ID NO: 3,
  b) a first light chain (LC) comprising a light chain variable region (LCVR) having the amino acid sequence of SEQ ID NO: 4,
  c) a second HC comprising a HCVR having the amino acid sequence of SEQ ID NO: 5, SEQ ID NO: 6, or SEQ ID NO: 7,
  d) a second LC comprising a LCVR having the amino acid sequence of SEQ ID NO: 8, SEQ ID NO: 9, or SEQ ID NO: 10;
and wherein, the first LC forms an inter-chain disulfide bond with the first HC, the second LC forms an inter-chain disulfide bond with the second HC, and the first HC forms two inter-chain disulfide bonds with the second HC, and the first HC and second HC are human IgG1 isotype.

The present invention further provides an antibody wherein the second HC comprises a HCVR having the amino acid sequence of SEQ ID NO: 5, and the second LC comprises a LCVR having the amino acid sequence of SEQ ID NO: 8. The present invention further provides an antibody wherein the second HC comprises a HCVR having the amino acid sequence of SEQ ID NO: 6, and the second LC comprises a LCVR having the amino acid sequence of SEQ ID NO: 9. The present invention further provides an antibody, wherein the second HC comprises a HCVR having the amino acid sequence of SEQ ID NO: 7, and the second LC comprises a LCVR having the amino acid sequence of SEQ ID NO: 10.

The present invention further provides an antibody, wherein:
  a) the first HC comprises the amino acid sequences of SEQ ID NO: 19 and SEQ ID NO: 22,
  b) the second HC comprises the amino acid sequences of SEQ ID NO: 23 and SEQ ID NO: 26,
  c) the first LC comprises the amino acid sequence of SEQ ID NO: 27, and
  d) the second LC comprises the amino acid sequence of SEQ ID NO: 28.

The present invention provides an antibody that binds human PD-L1 (SEQ ID NO: 1) and human TIM-3 (SEQ ID NO: 2) comprising:
  a) a first HC comprising the amino acid sequences of SEQ ID NO: 3, SEQ ID NO: 19 and SEQ ID NO: 22,
  b) a first LC comprising the amino acid sequences of SEQ ID NO: 4, and SEQ ID NO: 27,
  c) a second HC comprising the amino acid sequences of SEQ ID NO: 5, SEQ ID NO: 23 and SEQ ID NO: 26,
  d) a second LC comprising the amino acid sequences of SEQ ID NO: 8, and SEQ ID NO: 28;
and wherein, the first LC forms an inter-chain disulfide bond with the first HC, the second LC forms an inter-chain disulfide bond with the second HC, and the first HC forms two inter-chain disulfide bonds with the second HC, and the first HC and second HC are human IgG1 isotype.

The present invention provides an antibody that binds human PD-L1 (SEQ ID NO: 1) and human TIM-3 (SEQ ID NO: 2) comprising:
  a) a first HC comprising the amino acid sequences of SEQ ID NO: 3, SEQ ID NO: 19 and SEQ ID NO: 22,
  b) a first LC comprising the amino acid sequences of SEQ ID NO: 4, and SEQ ID NO: 27,
  c) a second HC comprising the amino acid sequences of SEQ ID NO: 6, SEQ ID NO: 23 and SEQ ID NO: 26,
  d) a second LC comprising the amino acid sequences of SEQ ID NO: 9, and SEQ ID NO: 28;
and wherein, the first LC forms an inter-chain disulfide bond with the first HC, the second LC forms an inter-chain disulfide bond with the second HC, and the first HC forms two inter-chain disulfide bonds with the second HC, and the first HC and second HC are human IgG1 isotype.

The present invention provides an antibody that binds human PD-L1 (SEQ ID NO: 1) and human TIM-3 (SEQ ID NO: 2) comprising:
  a) a first HC comprising the amino acid sequences of SEQ ID NO: 3, SEQ ID NO: 19 and SEQ ID NO: 22,
  b) a first LC comprising the amino acid sequences of SEQ ID NO: 4, and SEQ ID NO: 27,
  c) a second HC comprising the amino acid sequences of SEQ ID NO: 7, SEQ ID NO: 23 and SEQ ID NO: 26,
  d) a second LC comprising the amino acid sequences of SEQ ID NO: 10, and SEQ ID NO: 28;
and wherein, the first LC forms an inter-chain disulfide bond with the first HC, the second LC forms an inter-chain disulfide bond with the second HC, and the first HC forms two inter-chain disulfide bonds with the second HC, and the first HC and second HC are human IgG1 isotype.

The present invention further provides an antibody that binds human PD-L1 (SEQ ID NO: 1) and human TIM-3 (SEQ ID NO: 2), wherein:
  a) the first HC comprises the amino acid sequences of SEQ ID NO: 20 and SEQ ID NO: 21, and
  b) the second HC comprises the amino acid sequences of SEQ ID NO: 24 and SEQ ID NO: 25.

For SEQ ID NOs: 19-28, Table 1 maps where the sequences correlate on the antibody. For SEQ ID NOs: 3-10, Table 2 maps where the sequences correlate on the antibody.

The present invention provides an antibody that binds human PD-L1 (SEQ ID NO: 1) and human TIM-3 (SEQ ID NO: 2) comprising two light chains (LC) and two heavy chains (HC), wherein:
  a) the first LC has the amino acid sequence of SEQ ID NO: 12,
  b) the first HC has the amino acid sequence of SEQ ID NO: 11,
  c) the second LC has the amino acid sequence of SEQ ID NO: 16, SEQ ID NO: 17, or SEQ ID NO: 18, and
  d) the second HC has the amino acid sequence of SEQ ID NO: 13, SEQ ID NO: 14, or SEQ ID NO: 15.

The present invention provides an antibody comprising two light chains (LC) and two heavy chains (HC), wherein:
  a) the first LC has the amino acid sequence of SEQ ID NO: 12,
  b) the first HC has the amino acid sequence of SEQ ID NO: 11,
  c) the second LC has the amino acid sequence of SEQ ID NO: 16, SEQ ID NO: 17, or SEQ ID NO: 18, and
  d) the second HC has the amino acid sequence of SEQ ID NO: 13, SEQ ID NO: 14, or SEQ ID NO: 15.

The present invention provides an antibody that binds human PD-L1 (SEQ ID NO: 1) and human TIM-3 (SEQ ID NO: 2) comprising two light chains (LC) and two heavy chains (HC), wherein:
  a) the first LC has the amino acid sequence of SEQ ID NO: 12, and the first HC has the amino acid sequence of SEQ ID NO: 11, and
  b) the second LC and the second HC have the amino acid sequences of SEQ ID NO: 16 and SEQ ID NO: 13, SEQ ID NO: 17 and SEQ ID NO: 14, or SEQ ID NO: 18 and SEQ ID NO: 15, respectively.

The present invention further provides an antibody, wherein the second LC has the amino acid sequence of SEQ ID NO: 16, and the second HC has the amino acid sequence of SEQ ID NO: 13. The present invention further provides an antibody, wherein the second LC has the amino acid sequence of SEQ ID NO: 17, and the second HC has the amino acid sequence of SEQ ID NO: 14. The present invention further provides an antibody, wherein the second LC has the amino acid sequence of SEQ ID NO: 18, and the second HC has the amino acid sequence of SEQ ID NO: 15.

The present invention provides a half-antibody that binds human PD-L1 (SEQ ID NO: 1) comprising a LC and a HC, wherein the LC has the amino acid sequence of SEQ ID NO: 12, and the HC has the amino acid sequence of SEQ ID NO: 11.

The present invention provides a half-antibody that binds human TIM-3 (SEQ ID NO: 2) comprising a LC and a HC, wherein the LC and the HC have the amino acid sequences of SEQ ID NO: 16 and SEQ ID NO: 13, SEQ ID NO: 17 and SEQ ID NO: 14, or SEQ ID NO: 18 and SEQ ID NO: 15, respectively.

TABLE 1

Sequences mapped to region of IgG1 heavy chain or light chain

| SEQ ID NO | Region | Amino acid positions of Antibody C that correlates with sequence |
| --- | --- | --- |
| 19 | CH1 | 128-190 of PD-L1 antibody heavy chain (SEQ ID NO: 11) |
| 20 | CH2 | 237-271 of PD-L1 antibody heavy chain (SEQ ID NO: 11) |
| 21 | CH2 | 330-340 of PD-L1 antibody heavy chain (SEQ ID NO: 11) |
| 22 | CH3 | 350-410 of PD-L1 antibody heavy chain (SEQ ID NO: 11) |
| 23 | CH1 | 128-190 of TIM-3 antibody heavy chain (SEQ ID NO: 15) |
| 24 | CH2 | 231-265 of TIM-3 antibody heavy chain (SEQ ID NO: 15) |
| 25 | CH2 | 330-340 of TIM-3 antibody heavy chain (SEQ ID NO: 15) |
| 26 | CH3 | 350-410 of TIM-3 antibody heavy chain (SEQ ID NO: 15) |
| 27 | CL | 131-181 of PD-L1 antibody light chain (SEQ ID NO: 12) |
| 28 | CL | 131-181 of TIM-3 antibody light chain (SEQ ID NO: 18) |

The present invention provides a mammalian cell comprising a DNA molecule comprising a polynucleotide sequence encoding polypeptides having the amino acid sequences of SEQ ID NO: 11, SEQ ID NO: 15, SEQ ID NO: 12, and SEQ ID NO: 18, wherein the cell is capable of expressing an antibody of the present invention.

The present invention provides a mammalian cell comprising a first DNA molecule and a second DNA molecule, wherein the first DNA molecule comprises a polynucleotide sequence encoding polypeptides having the amino acid sequence of SEQ ID NO: 11 and SEQ ID NO: 12, and wherein the second DNA molecule comprises a polynucleotide sequence encoding polypeptides having the amino acid sequence of SEQ ID NO: 15 and SEQ ID NO: 18, wherein the cell is capable of expressing an antibody of the present invention.

The present invention provides a mammalian cell comprising a first DNA molecule, a second DNA molecule, a third DNA molecule, and a fourth DNA molecule, wherein the first DNA molecule comprises a polynucleotide sequence encoding a polypeptide having the amino acid sequence of SEQ ID NO: 11, the second DNA molecule comprises a polynucleotide sequence encoding a polypeptide having the amino acid sequence of SEQ ID NO: 12, the third DNA molecule comprises a polynucleotide sequence encoding a polypeptide having the amino acid sequence of SEQ ID NO: 15, and the fourth DNA molecule comprises a polynucleotide sequence encoding a polypeptide having the amino acid sequence of SEQ ID NO: 18, wherein the cell is capable of expressing an antibody of the present invention.

The present invention provides a process for producing an antibody of the present invention comprising cultivating a mammalian cell of the present invention under conditions such that the antibody is expressed, and recovering the expressed antibody.

The present invention provides an antibody produced by a process of the present invention.

The present invention provides an antibody produced by cultivating a mammalian cell comprising a DNA molecule comprising a polynucleotide sequence encoding polypeptides having the amino acid sequences of SEQ ID NO: 11, SEQ ID NO: 15, SEQ ID NO: 12, and SEQ ID NO: 18 under conditions such that the antibody is expressed, and recovering the expressed antibody.

The present invention provides an antibody produced by cultivating a mammalian cell comprising a first DNA molecule and a second DNA molecule, wherein the first DNA molecule comprises a polynucleotide sequence encoding polypeptides having the amino acid sequence of SEQ ID NO: 11 and SEQ ID NO: 12, and wherein the second DNA molecule comprises a polynucleotide sequence encoding polypeptides having the amino acid sequence of SEQ ID NO: 15 and SEQ ID NO: 18 under conditions such that the antibody is expressed, and recovering the expressed antibody.

The present invention provides a pharmaceutical composition, comprising an antibody of the present invention and an acceptable carrier, diluent, or excipient.

The present invention provides a method of treating cancer, comprising administering to a patient in need thereof, an effective amount of an antibody of the present invention. The present invention further provides a method of treating cancer, comprising administering to a patient in need thereof, an effective amount of an antibody of the present invention, wherein the cancer is melanoma, lung cancer, head and neck cancer, liver cancer, colorectal cancer, pancreatic cancer, gastric cancer, kidney cancer, bladder cancer, prostate cancer, breast cancer, ovarian cancer, endometrial cancer, esophageal cancer, soft tissue sarcoma, cholangiocarcinoma, or hepatocellular carcinoma.

The present invention provides a method of treating cancer, wherein the cancer is melanoma. The present invention further provides a method of treating cancer, wherein the cancer is lung cancer. The present invention further provides a method of treating cancer, wherein the lung cancer is non-small cell lung cancer, small cell lung cancer, or mesothelioma. The present invention further provides a method of treating cancer, wherein the cancer is head and neck cancer. The present invention further provides a method of treating cancer, wherein the cancer is liver cancer. The present invention further provides a method of treating cancer, wherein the cancer is colorectal cancer. The present invention further provides a method of treating cancer, wherein the cancer is pancreatic cancer. The present invention further provides a method of treating cancer, wherein the cancer is gastric cancer. The present invention further provides a method of treating cancer, wherein the cancer is kidney cancer. The present invention further provides a method of treating cancer, wherein the cancer is bladder cancer. The present invention further provides a method of treating cancer, wherein the cancer is prostate cancer. The present invention further provides a method of treating cancer, wherein the cancer is breast cancer. The present invention further provides a method of treating cancer, wherein the cancer is ovarian cancer. The present invention further provides a method of treating cancer, wherein the cancer is endometrial cancer. The present invention further provides a method of treating cancer, wherein the cancer is esophageal cancer. The present invention further provides a method of treating cancer, wherein the cancer is soft tissue sarcoma. The present invention further provides a method of treating cancer, wherein the cancer is cholangiocarcinoma. The present invention further provides a method of treating cancer, wherein the cancer is hepatocellular carcinoma.

The present invention further provides methods comprising the administration of an effective amount of the antibody of the present invention in simultaneous, separate, or sequential combination with one or more standard of care agents selected from the group consisting of cisplatin, carboplatin, dacarbazine, liposomal doxorubicin, docetaxel, cyclophosphamide and doxorubicin, navelbine, eribulin, paclitaxel, paclitaxel protein-bound particles for injectable suspension, ixabepilone, capecitabine, FOLFOX (leucovorin, fluorouracil, and oxaliplatin), FOLFIRI (leucovorin, fluorouracil, and irinotecan), gemcitabine, topotecan, liposomal irinotecan, pemetrexed, and cetuximab.

The present invention further provides methods comprising the administration of an effective amount of the antibody of the present invention in simultaneous, separate, or sequential combination with one or more antitumor agents selected from the group consisting of nivolumab, ipilimumab, pidilizumab, pembrolizumab, tremelimumab, urelumab, lirilumab, atezolizumab, epacadostat, and durvalumab.

The present invention further provides methods comprising the administration of an effective amount of the antibody of the present invention comprising simultaneous, separate, or sequential combination with ionizing radiation.

The present invention provides an antibody of the present invention, for use in therapy. The present invention provides an antibody of the present invention, for use in the treatment of cancer. The present invention provides an antibody of the present invention, for use in the treatment of cancer, wherein the cancer is melanoma, lung cancer, head and neck cancer, liver cancer, colorectal cancer, pancreatic cancer, gastric cancer, kidney cancer, bladder cancer, prostate cancer, breast cancer, ovarian cancer, endometrial cancer, esophageal cancer, soft tissue sarcoma, cholangiocarcinoma, or hepatocellular carcinoma.

The present invention provides an antibody of the present invention, for use in the treatment of melanoma. The present invention provides an antibody of the present invention, for use in the treatment of lung cancer. The present invention further provides an antibody of the present invention, wherein the lung cancer is non-small cell lung cancer, small cell lung cancer, or mesothelioma. The present invention provides an antibody of the present invention, for use in the treatment of head and neck cancer. The present invention provides an antibody of the present invention, for use in the treatment of liver cancer. The present invention provides an antibody of the present invention, for use in the treatment of colorectal cancer. The present invention provides an antibody of the present invention, for use in the treatment of pancreatic cancer. The present invention provides an antibody of the present invention, for use in the treatment of gastric cancer. The present invention provides an antibody of the present invention, for use in the treatment of kidney cancer. The present invention provides an antibody of the present invention, for use in the treatment of bladder cancer. The present invention provides an antibody of the present invention, for use in the treatment of prostate cancer. The present invention provides an antibody of the present invention, for use in the treatment of breast cancer. The present invention provides an antibody of the present invention, for use in the treatment of ovarian cancer. The present invention provides an antibody of the present invention, for use in the treatment of endometrial cancer. The present invention provides an antibody of the present invention, for use in the treatment of esophageal cancer. The present invention provides an antibody of the present invention, for use in the treatment of soft tissue sarcoma. The present invention provides an antibody of the present invention, for use in the treatment of cholangiocarcinoma. The present invention provides an antibody of the present invention, for use in the treatment of hepatocellular carcinoma.

The present invention provides the antibody of the present invention for use in simultaneous, separate, or sequential combination with one or more standard of care agents selected from the group consisting of cisplatin, carboplatin, dacarbazine, liposomal doxorubicin, docetaxel, cyclophosphamide and doxorubicin, navelbine, eribulin, paclitaxel, paclitaxel protein-bound particles for injectable suspension, ixabepilone, capecitabine, FOLFOX (leucovorin, fluorouracil, and oxaliplatin), FOLFIRI (leucovorin, fluorouracil, and irinotecan), gemcitabine, topotecan, liposomal irinotecan, pemetrexed, and cetuximab, in the treatment of cancer.

The present invention provides the antibody of the present invention for use in simultaneous, separate, or sequential combination with one or more antitumor agents selected from the group consisting of nivolumab, ipilimumab, pidilizumab, pembrolizumab, tremelimumab, urelumab, lirilumab, atezolizumab, epacadostat, and durvalumab, in the treatment of cancer.

The present invention provides the antibody of the present invention for use in simultaneous, separate, or sequential combination with ionizing radiation, in the treatment of cancer.

The present invention provides a pharmaceutical composition for use in treating cancer, comprising an effective amount of an antibody of the present invention. The present invention further provides a pharmaceutical composition for use in treating cancer, comprising an effective amount of an antibody of the present invention, wherein the cancer is melanoma, lung cancer, head and neck cancer, liver cancer, colorectal cancer, pancreatic cancer, gastric cancer, kidney cancer, bladder cancer, prostate cancer, breast cancer, ovarian cancer, endometrial cancer, esophageal cancer, soft tissue sarcoma, cholangiocarcinoma, or hepatocellular carcinoma. The present invention further provides a pharmaceutical composition for use in treating cancer, comprising an effective amount of an antibody of the present invention, wherein the lung cancer is non-small cell lung cancer, small cell lung cancer, or mesothelioma.

The present invention provides a pharmaceutical composition for use in treating melanoma, comprising an effective amount of an antibody of the present invention. The present invention provides a pharmaceutical composition for use in treating lung cancer, comprising an effective amount of an antibody of the present invention. The present invention provides a pharmaceutical composition for use in treating head and neck cancer, comprising an effective amount of an antibody of the present invention. The present invention provides a pharmaceutical composition for use in treating liver cancer, comprising an effective amount of an antibody of the present invention. The present invention provides a pharmaceutical composition for use in treating colorectal cancer, comprising an effective amount of an antibody of the present invention. The present invention provides a pharmaceutical composition for use in treating pancreatic cancer, comprising an effective amount of an antibody of the present invention. The present invention provides a pharmaceutical composition for use in treating gastric cancer, comprising an effective amount of an antibody of the present invention. The present invention provides a pharmaceutical composition for use in treating kidney cancer, comprising an effective amount of an antibody of the present invention. The present invention provides a pharmaceutical composition for use in treating bladder cancer, comprising an effective amount of an antibody of the present invention. The present invention provides a pharmaceutical composition for use in treating prostate cancer, comprising an effective amount of an antibody of the present invention. The present invention provides a pharmaceutical composition for use in treating breast cancer, comprising an effective amount of an antibody of the present invention. The present invention provides a pharmaceutical composition for use in treating ovarian cancer, comprising an effective amount of an antibody of the present invention. The present invention provides a pharmaceutical composition for use in treating endometrial cancer, comprising an effective amount of an antibody of the present invention. The present invention provides a pharmaceutical composition for use in treating esophageal cancer, comprising an effective amount of an antibody of the present invention. The present invention provides a pharmaceutical composition for use in treating soft tissue sarcoma, comprising an effective amount of an antibody of the present invention. The present invention provides a pharmaceutical composition for use in treating cholangiocarcinoma, comprising an effective amount of an antibody of the present invention. The present invention provides a pharmaceutical composition for use in treating hepatocellular carcinoma, comprising an effective amount of an antibody of the present invention.

The present invention further provides a pharmaceutical composition for use in treating cancer, wherein said pharmaceutical composition is administered in simultaneous, separate, or sequential combination with one or more standard of care agents selected from the group consisting of cisplatin, carboplatin, dacarbazine, liposomal doxorubicin, docetaxel, cyclophosphamide and doxorubicin, navelbine, eribulin, paclitaxel, paclitaxel protein-bound particles for injectable suspension, ixabepilone, capecitabine, FOLFOX (leucovorin, fluorouracil, and oxaliplatin), FOLFIRI (leucovorin, fluorouracil, and irinotecan), gemcitabine, topotecan, liposomal irinotecan, pemetrexed, and cetuximab.

The present invention further provides a pharmaceutical composition for use in treating cancer, wherein said pharmaceutical composition is administered in simultaneous, separate, or sequential combination with one or more antitumor agents selected from the group consisting of nivolumab, ipilimumab, pidilizumab, pembrolizumab, tremelimumab, urelumab, lirilumab, atezolizumab, epacadostat, and durvalumab.

The present invention further provides a pharmaceutical composition for use in treating cancer, wherein said pharmaceutical composition is administered in simultaneous, separate, or sequential combination with ionizing radiation.

The present invention provides the use of an antibody of the present invention for the manufacture of a medicament for the treatment of cancer. The present invention further provides the use of an antibody of the present invention for the manufacture of a medicament for the treatment of cancer, wherein the cancer is melanoma, lung cancer, head and neck cancer, liver cancer, colorectal cancer, pancreatic cancer, gastric cancer, kidney cancer, bladder cancer, prostate cancer, breast cancer, ovarian cancer, endometrial cancer, esophageal cancer, soft tissue sarcoma, cholangiocarcinoma, or hepatocellular carcinoma. The present invention further provides the use of an antibody of the present invention for the manufacture of a medicament for the treatment of cancer, wherein the lung cancer is non-small cell lung cancer, small cell lung cancer, or mesothelioma.

The present invention further provides the use of an antibody of the present invention in the manufacture of a medicament for the treatment of cancer wherein said medicament is to be administered simultaneously, separately, or sequentially with one or more standard of care agents selected from the group consisting of cisplatin, carboplatin, dacarbazine, liposomal doxorubicin, docetaxel, cyclophosphamide and doxorubicin, navelbine, eribulin, paclitaxel, paclitaxel protein-bound particles for injectable suspension, ixabepilone, capecitabine, FOLFOX (leucovorin, fluorouracil, and oxaliplatin), FOLFIRI (leucovorin, fluorouracil, and irinotecan), gemcitabine, topotecan, liposomal irinotecan, pemetrexed, and cetuximab.

The present invention further provides the use of an antibody of the present invention in the manufacture of a medicament for the treatment of cancer wherein said medicament is to be administered simultaneously, separately, or sequentially with one or more antitumor agents selected from the group consisting of nivolumab, ipilimumab, pidilizumab, pembrolizumab, tremelimumab, urelumab, lirilumab, atezolizumab, epacadostat, and durvalumab.

The present invention provides the use of an antibody of the present invention in the manufacture of a medicament for the treatment of cancer wherein said medicament is to be administered simultaneously, separately, or sequentially with ionizing radiation.

An antibody of the present invention is an engineered, non-naturally occurring polypeptide complex. A DNA molecule of the present invention is a non-naturally occurring DNA molecule that comprises a polynucleotide sequence encoding a polypeptide having the amino acid sequence of one of the polypeptides in an antibody of the present invention.

The antibody of the present invention is an IgG type antibody and has "heavy" chains and "light" chains that are cross-linked via intra- and inter-chain disulfide bonds. Each heavy chain is comprised of an N-terminal HCVR and a heavy chain constant region ("HCCR"). Each light chain is comprised of a LCVR and a light chain constant region ("LCCR"). Light chains each form disulfide bonds with a heavy chain, and the two heavy chains form two disulfide bonds between each other.

The constant region of the heavy chains contains CH1, CH2, and CH3 domains. CH1 comes after the HCVR; the CH1 and HCVR form the heavy chain portion of a Fab. CH2 comes after the hinge region and before CH3. CH3 comes after CH2 and is at the carboxy-terminal end of the heavy chain.

The constant region of the light chains contains one domain, CL. CL comes after the LCVR; the CL and LCVR form the light chain portion of a Fab.

Antibodies of the present invention are heterodimeric in that each arm of the antibody exhibits selective monovalent binding to its cognate antigen due to two different heavy chains and two different light chains forming the antibody. In the present invention one arm of the antibody binds human PD-L1 (SEQ ID NO: 1), and the other arm binds human TIM-3 (SEQ ID NO: 2). In order to ensure proper assembly of these bispecific antibodies, mutations are incorporated into the sequence of the heavy chains within the CH1 and CH3 region and into the sequence of the light chains within the light chain constant region. The CH1 and LC mutations are made to favor native pairing of the requisite light chain and heavy chain pairs and disfavor light chain mispairing. The CH3 mutations are made to favor heterodimeric pairing of the two distinct heavy chains and disfavor formation of homodimers. Mutations in the CH3 region of the anti-PD-L1 portion of the antibody preferably includes positions 356, 372, 398, and 400 as numbered by absolute position in SEQ ID NO: 11 (positions 350, 366, 392, and 394 if using EU numbering). Mutations in the CH3 region of the anti-TIM-3 portion of the antibody preferably includes positions 350, 351, 356, 405, and 407 as numbered by absolute position in SEQ ID NO: 15 (positions 350, 351, 405, and 407 if using EU numbering). Mutations in the CH1 region of the anti-PD-L1 portion of the antibody preferably includes positions 189 as numbered by absolute position in SEQ ID NO: 11 (position 183 if using EU numbering). Mutations in the CH1 region of the anti-TIM-3 portion of the antibody preferably includes positions 128, 147, 175, and 183 as numbered by absolute position in SEQ ID NO: 15 (positions 128, 147, 175, and 183 if using EU numbering).

Mutations in the CL region of the anti-PD-L1 portion of the antibody preferably includes positions 179 and 181 as numbered by absolute position in SEQ ID NO: 11 (positions 176 and 178 if using EU numbering). Mutations in the CL region of the anti-TIM-3 portion of the antibody preferably includes positions 131, 133, 176, and 178 as numbered by absolute position in SEQ ID NO: 15 (positions 131, 133, 176, and 178 if using EU numbering).

In certain antibodies of the present invention, heavy chain heterodimeric pairing mutations yield a CH3 thermal stability greater than 80° C., which is comparable to native antibodies (Table 1 and Von Kreudenstein, et al., 2014).

When expressed in certain biological systems, antibodies having Fc sequences are glycosylated in the Fc region. Typically, glycosylation occurs in the Fc region of the antibody at a highly conserved N-glycosylation site. N-glycans typically attach to asparagine. Antibodies may be glycosylated at other positions as well.

Optionally, certain antibodies of the present invention contain an Fc portion which is derived from human IgG1. IgG1 is well known to bind to the proteins of the Fc-gamma receptor family (FcγR) as well as C1q. Interaction with these receptors can induce antibody-dependent cell cytotoxicity (ADCC) and complement-dependent cytotoxicity (CDC). Therefore, certain amino acid substitutions are introduced into IgG1 Fc for certain antibodies of the present invention, including Antibody A, B, and C, to ablate immune effector function. Mutations in the CH2 region of the anti-PD-L1 portion of the antibody may include positions 240, 241, and 271 as numbered by absolute position in SEQ ID NO: 11 (positions 234, 235, and 265 if using EU numbering). Mutations in the CH2 region of the anti-TIM-3 portion of the antibody may include positions 234, 235, and 265 as numbered by absolute position in SEQ ID NO: 15 (positions 234, 235, and 265 if using EU numbering).

An isolated DNA encoding a HCVR region can be converted to a full-length heavy chain gene by operably linking the HCVR-encoding DNA to another DNA molecule encoding heavy chain constant regions. The sequences of human, as well as other mammalian, heavy chain constant region genes are known in the art. DNA fragments encompassing these regions can be obtained e.g., by standard PCR amplification.

An isolated DNA encoding a LCVR region may be converted to a full-length light chain gene by operably linking the LCVR-encoding DNA to another DNA molecule encoding a light chain constant region. The sequences of human, as well as other mammalian, light chain constant region genes are known in the art. DNA fragments encompassing these regions can be obtained by standard PCR amplification. The light chain constant region can be a kappa or lambda constant region. Preferably for antibodies of the present invention, the light chain constant region of the anti-PD-L1 portion of the antibody is a lambda light chain and the light chain constant region of the anti-TIM-3 portion of the antibody is a kappa light chain.

The polynucleotides of the present invention will be expressed in a host cell after the sequences have been operably linked to an expression control sequence. The expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences.

The antibody of the present invention may readily be produced in mammalian cells such as CHO, NS0, HEK293 or COS cells. The host cells are cultured using techniques well known in the art.

The vectors containing the polynucleotide sequences of interest (e.g., the polynucleotides encoding the polypeptides of the antibody and expression control sequences) can be transferred into the host cell by well-known methods, which vary depending on the type of cellular host.

Various methods of protein purification may be employed and such methods are known in the art and described, for example, in Deutscher, *Methods in Enzymology* 182: 83-89 (1990) and Scopes, *Protein Purification: Principles and Practice*, 3rd Edition, Springer, NY (1994).

In another embodiment of the present invention, the antibody, or the nucleic acids encoding the same, is provided in isolated form. As used herein, the term "isolated" refers to a protein, peptide, or nucleic acid which is free or substantially free from any other macromolecular species found in a cellular environment. "Substantially free" as used herein means the protein, peptide, or nucleic acid of interest comprises more than 80% (on a molar basis) of the macromolecular species present, preferably more than 90%, and more preferably more than 95%.

The antibody of the present invention, or pharmaceutical compositions comprising the same, may be administered by parenteral routes (e.g., subcutaneous and intravenous). An antibody of the present invention may be administered to a patient alone with pharmaceutically acceptable carriers, diluents, or excipients in single or multiple doses. Pharmaceutical compositions of the present invention can be prepared by methods well known in the art (e.g., *Remington: The Science and Practice of Pharmacy*, 22$^{nd}$ ed. (2012), A. Loyd et al., Pharmaceutical Press) and comprise an antibody, as disclosed herein, and one or more pharmaceutically acceptable carriers, diluents, or excipients.

The term "treating" (or "treat" or "treatment") refers to slowing, interrupting, arresting, alleviating, stopping, reducing, or reversing the progression or severity of an existing symptom, disorder, condition, or disease.

"Binds" as used herein in reference to the affinity of an antibody for human PD-L1 (SEQ ID NO: 1), human TIM-3 (SEQ ID NO: 2), or both is intended to mean, unless indicated otherwise, a $K_D$ of less than about $1\times10^{-6}$ M, preferably, less than about $1\times10^{-9}$ M as determined by common methods known in the art, including by use of a surface plasmon resonance (SPR) biosensor at 37° C. essentially as described herein.

"Effective amount" means the amount of an antibody of the present invention or pharmaceutical composition comprising an antibody of the present invention that will elicit the biological or medical response of or desired therapeutic effect on a tissue, system, animal, mammal or human that is being sought by the researcher, medical doctor, or other clinician. An effective amount of the antibody may vary according to factors such as the disease state, age, sex, and weight of the individual, and the ability of the antibody to elicit a desired response in the individual. An effective amount is also one in which any toxic or detrimental effect of the antibody is outweighed by the therapeutically beneficial effects.

This invention is further illustrated by the following non-limiting example.

Example 1: Antibody Expression and Purification

The polypeptides of the variable regions of the heavy chain and light chain, the complete heavy chain and light chain amino acid sequences of Antibody A, Antibody B, and Antibody C, and the nucleotide sequences encoding the same, are listed below in the section entitled "Amino Acid and Nucleotide Sequences." In addition, the SEQ ID NOs for the light chain, heavy chain, light chain variable region, and heavy chain variable region of Antibody A, B, and C are shown in Table 2.

The antibodies of the present invention, including, but not limited to, Antibody A, Antibody B, and Antibody C, can be made and purified essentially as follows. An appropriate host cell, such as CHO, can be either transiently or stably transfected with an expression system for secreting antibodies using a quad vector, dual vectors, or four single vectors at a ratio of 20HC anti-TIM-3:10HC anti-PD-L1:24LC anti-TIM-3:46LC anti-PD-L1. SEQ ID NO: 29 to SEQ ID NO: 32 are DNA sequences for the light chains and heavy chains of Antibody C; the PD-L1 antibody light chain has an internal intron to increase expression levels relative to the TIM-3 light chain. Clarified media, into which the antibody has been secreted, may be purified using any of many commonly-used techniques. For example, the medium may be conveniently applied to a MabSelect column (GE Healthcare), or KappaSelect column (GE Healthcare) for Fab fragment, that has been equilibrated with a compatible buffer, such as phosphate buffered saline (pH 7.4). The column may be washed to remove nonspecific binding components. The bound antibody may be eluted, for example, by pH gradient (such as 20 mM Tris buffer pH 7 to 10 mM sodium citrate buffer pH 3.0, or phosphate buffered saline pH 7.4 to 100 mM glycine buffer pH 3.0). Antibody fractions may be detected, such as by SDS-PAGE, and then may be pooled. Soluble aggregate and multimers may be effectively removed by common techniques, including size exclusion, hydrophobic interaction, ion exchange, multimodal, or hydroxyapatite chromatography. The antibody may be concentrated and/or sterile filtered using common techniques. The product may be immediately frozen at −70° C. or may be lyophilized.

TABLE 2

SEQ ID NOs

| | Antibody A | Antibody B | Antibody C |
|---|---|---|---|
| HCVR1 - anti-PD-L1 | 3 | 3 | 3 |
| HCVR2 - anti-TIM-3 | 5 | 6 | 7 |
| LCVR1 - anti-PD-L1 | 4 | 4 | 4 |
| LCVR2 - anti-TIM-3 | 8 | 9 | 10 |
| Heavy chain 1 - anti-PD-L1 | 11 | 11 | 11 |
| Heavy chain 2 - anti-TIM-3 | 13 | 14 | 15 |
| Light chain 1 - anti-PD-L1 | 12 | 12 | 12 |
| Light chain 2 - anti-TIM-3 | 16 | 17 | 18 |

Assays
In Vitro Binding of Antibodies

With a heterodimeric bispecific antibody, one arm of the antibody (one light chain and one heavy chain) monovalently binds one antigen, and the second arm of the antibody (one light chain and one heavy chain) monovalently binds the second antigen. The ability of antibodies of the present invention to maintain comparable binding to each antigen when compared to the parental antibodies that bivalently bind antigen can be assessed by a Biacore assay.

The binding kinetics and affinity of Antibody C and its parental antibodies to the corresponding antigens TIM-3 and PD-L1 were analyzed by surface plasmon resonance (SPR) using BIAcore T200 biosensor instrument (GE Healthcare) at 37° C. The human Fab was immobilized on CM5 sensor chip using amine coupling at immobilization level 7000 to 9000 RU. Antibody samples were diluted in HBS-EP+ buffer and injected at a flow rate of 30 μL/min. A serial concentrations of human TIM-3 single arm antigen (TIM-3-SAG) and Fc tagged PD-L1 (PD-L1-Fc) were then injected for 180 seconds followed by a dissociation time of 1200 seconds. Sensorgrams were evaluated using Biacore T200 evaluation software 3.0 and calculation of association (Ka) and dissociation (Kd) rate constants was based on a 1:1 Langmuir binding model fit. The equilibrium dissociation constant (KD) or binding affinity constant was calculated from the ratio of kinetic rate constants Kd/Ka.

Monovalent antigen binding to PD-L1 for the Fab of Antibody A was $6.5 \times 10^{-10}$ M and was comparable to the bivalent binding of PD-L1 by the Fab of the parental anti-PD-L1 antibody. The monovalent PD-L1 binding of the Fabs of Antibody B and C were also comparable to the Fab of the parental anti-PD-L1 antibody.

Monovalent antigen binding to TIM-3 for the Fab of Antibody A was $2.53 \times 10^{-9}$ M and was approximately 33-fold lower than the bivalent binding affinity of the parental anti-TIM-3 antibody. The Fab of Antibody B had a Kd of $1.91 \times 10^{-10}$ M against TIM-3, and the Fab of Antibody C had a Kd of $1.11 \times 10^{-10}$ M against TIM-3. The monovalent Fab binding of Antibody B was three-fold lower affinity than the bivalent binding affinity of the parental anti-TIM-3 antibody, whereas the monovalent Fab binding of Antibody C was comparable to the bivalent binding affinity of the parental.

Thermal Stability

With a heterodimeric bispecific antibody, pairing of two different heavy chains and selective pairing of cognate light chains with each respective heavy chain is required. The ability of antibodies of the present invention to maintain stability comparable to a native antibody can be tested by DSC analysis.

Studies were performed at 1 mg/mL in PBS using a MicroCal VP-Capillary DSC (Serial#11.05083.CAP). All samples were scanned within the temperature range of 25-100° C. with a scan rate of 60° C./hour. The solutions were pressurized at about 60 psi in the capillaries during each scan. For each protein, buffer/buffer scan was subtracted from buffer/protein scan and the thermogram was normalized for protein concentration. Baseline correction was performed and the midpoint of each thermal denaturation (Tm) was obtained from peaks maximum.

In experiments performed essentially as described in this assay, DSC analysis of Antibody C showed thermal stability ($Tm_1$ 67° C., $Tm_2$ 76° C., $Tm_3$ 83° C.) with comparable unfolding temperatures as the parental antibodies (anti-PD-L1 Ab: $Tm_1$ 67° C., $Tm_2$ 75° C., $Tm_3$ 82° C., anti-TIM-3 Ab: $Tm_1$ 64° C., $Tm_2$ 85° C.).

Simultaneously Binding to PD-L1 and TIM-3 as Measured by ELISA

The ability for antibodies of the present invention to bind PD-L1 and TIM-3 simultaneously can be measured in a sandwich ELISA assay. TIM-3-Fc protein can be coated on the plate to test binding of antibodies of the present invention to TIM-3, but signal is only generated if plate-bound antibodies also bind soluble biotinylated PD-L1-Fc.

For the binding assay, a 96 well (Immulon 2HB) plate was coated with 50 μl/well of 1 μg/ml human TIM-3-Fc, at 4° C., overnight. Plate was then washed three times with PBS containing 0.2% Tween-20, and blocked with 250 μl/well of PBS with 3% BSA for 1 hr at room temperature. Blocking buffer was removed and 50 μl of titrated antibodies, starting at 200 nM, were added to the plate and incubated for 1 hr at room temperature. Plate was then washed three times with PBS containing 0.2% Tween-20, and 50 μl of 100 ng/ml human PD-L1 biotin was added and incubated for 1 hr at room temperature. Plate was then washed three times with PBS containing 0.2% Tween-20, and 50 μl of Strep HRP (Jackson Immuno 106-030-084), diluted 1:5000, was added and incubated for 1 hr at room temperature. Plate was then washed three times with PBS containing 0.2% Tween-20 and developed using 100 μl/well of 1:1 TMB substrate solution A and B (KPL) for 10 mins at room temperature. Reaction was stopped with 100 ul/well of 0.1 N $H_2SO_4$ and read on Spectramax plate reader. Data was graphed using GraphPad Prism.

In experiments performed essentially as described in this assay, Antibody C produced signal that increased with the concentration of Antibody C demonstrating that Antibody C binds human PD-L1 and TIM-3 simultaneously under these conditions. A control TIM-3 antibody alone produced only a background signal.

Antibody C Binds to PD-L1 and TIM-3 Targets Simultaneously on Cell Surface

The ability for antibodies of the present invention to simultaneously engage TIM-3 and PD-L1 proteins on the cell surface can be tested in a live cell reporter assay to measure TIM-3:PD-L1 Heterotypic Receptor Association (HRA) (DiscoverX, Fremont, Calif.). The HRA assay is based on enzyme fragment complementation and employs two recombinant β-galactosidase fragments which are individually catalytically inactive and show little affinity for each other. When added as fusion partners to proteins that do bind each other, the two fragments can be brought into proximity to reconstitute a functional (3-galactosidase enzyme. Enzyme activity is monitored by light produced during cleavage of a chemiluminescent substrate.

For the assay, U2OS cells were serially transfected with constructs coding for TIM-3 (1-223)-PK and PD-L1(1-259)-EA (PK=ProLink β-galactosidase fragment, EA=Enzyme Acceptor fragment). U2OS cells were chosen for their ability to tolerate ectopic membrane protein expression and TIM-3, PD-L1 constructs were designed to eliminate most of the intracellular domains and potential complications such as receptor internalization and signal-induced clustering.

Cells from stable U2OS TIM-3(1-223)-PK PD-L1(1-259)-EA pools were plated in quadruplicate on 384 well plates (5000 cells/well). A dilution series of Antibody C and corresponding parental anti-TIM-3 and anti-PD-L1 antibodies were added to the cells and incubated overnight (16 hours) at 37° C./5% $CO_2$. Detection reagents containing lysis buffer and enzyme substrate were then added to the cells and the plate read on an Envision luminometer.

In experiments performed essentially as described in this assay, Antibody C produces a titratable increase in signal with an EC50 of approximately 2 nM, while the corresponding single specificity monoclonal antibodies to TIM-3 and PD-L1 are completely inactive. These data indicate Antibody C can simultaneously engage both TIM-3 and PD-L1 on the cell surface under these conditions.

Antibody C Bridges TIM-3 Expressing Cells with PD-L1 Expressing Cells

The ability for antibodies of the present invention to bridge TIM-3 and PD-L1 expressing cells may be determined by flow cytometry analysis using transfected CHO expressing PD-L1 and DO11 cells expressing TIM-3. Briefly stated, CHO-PD-L1 and DO11-TIM-3 over-expressing cells may be differentially labeled with CFSE (carboxyfluorescein diacetate succinimidyl ester) (BD Horizon) or Cell Tracker Deep Red (CTDR/Thermo). DO11-TIM-3 and CHO-PDL1 cells are separately incubated for 30 minutes with a test antibody, such as Antibody C (on ice in PBS+1% BSA+0.09% sodium azide). Unbound antibodies may be removed by washing (2× with 200 μl PBS+1% BSA+0.09% sodium azide). CHO-PDL1 cells are incubated 2 hours with 45 μg/ml of the parental PD-L1 antibody or hIgG1 control on ice in PBS+1% BSA+0.09% sodium azide. DO11-TIM-3 cells are incubated 2 hours with 45 μg/ml of the parental TIM-3 antibody or huIgG4-PAA on ice in PBS+1% BSA+0.09% sodium azide. DO11-TIM-3/Antibody C cells are mixed with CHO-PDL1+ the parent PD-L1 antibody or hIgG1 at final concentration of 22.5 ug/ml. CHO-PDL1/Antibody C cells are mixed with DO11-TIM-3+ the parent of the TIM-3 antibody or huIgG4-PAA at a final concentration of 22.5 μg/ml. After an approximately 72 hour incubation at 4° C., cells are measured on Fortessa X20 (with HTS sampler) in channels suitable for CFSE and CTDR. Using FLOWJO® software (FlowJo, LLC, Ashland, Oreg.), double positive events (CFSE+/CTDR+) are gated and percentage of total events may be calculated and reported (for 2 replicate wells). Fits and statistics are generated with Graphpad Prism using nonlinear regression (variable slope, 4 parameters).

In experiments performed essentially as described above, Antibody C mediated cell bridging which was be detected as double positive events by flow cytometry. Binding of Antibody C to DO11-TIM-3 or CHO-PDL1 cells (with subsequent removal of unbound) and then mixing with CHO-PDL1 or DO11-TIM-3 cells, respectively, caused a dose dependent increase in double positive events relative to background (up to 4-fold increase compared to buffer only). This increase in double positive events was blocked by the addition of excess competing PD-L1 and/or TIM-3 mAbs at high concentration but not by matched non-specific IgG control, demonstrating specificity and dependence on target antigen expression.

In Vitro Functional Activity 1. hTIM-3 DO11 Cell Based Assay

The ability of antibodies of the present invention to alleviate suppression of T cells through TIM-3 inhibition can be measured in a DO11 in vitro assay.

For the hTIM-3 DO11 cell based assay, 50 μl of DO11 or hTIM-3 overexpressing DO11 cells at $2×10^4$ cells/well and 50 μl of A20 cells at $2×10^4$ cells/well were plated in a 96 well U bottom tissue culture plate (Greiner Cellstar, #651180), using RPMI 1640 media (Gibco, #11875-085). 50 μl of OVA (Sigma, #01641) was added at final concentration of 0.2 μM (diluted in media). 50 μl of serially diluted antibodies was added (diluted in media). Media was added to some wells to make the total volume 200 μl/well. Supernatant was collected after 18-22 hours and measured for mIL-2 using an ELISA kit (R&D, #SM2000).

In experiments performed essentially as described in this assay, Antibody C enhanced OVA antigen-specific T cell activation in a dose-dependent manner with EC50 of 4.366 nM as measured by increasing mIL-2 levels, but a human IgG control did not.

2. Mixed Leukocyte Reaction (MLR) Assay

The ability of antibodies of the present invention to block PD-L1 signals may be evaluated by measuring the release of cytokines during T-cell activation in an in vitro MLR assay. The levels of certain cytokines, such as IFN-γ, are expected to increase if T-cell activation is promoted by treatment with antibodies of the present invention.

For the MLR assay, monocytes were isolated from human PBMC (Allcells, # PB001) with human monocyte isolation kit II (Miltenyi, #130-091-153) and cultured for 7 days with 62.5 ng/ml GM-CSF and 20 ng/ml IL-4 to differentiate dendritic cells. 100 μl of $1×10^5$ CD4 T-cells isolated from PBMC (different donor from Allcells) with CD4 T-cell isolation kit (Miltenyi, cat#130-091-155) and $1×10^4$ monocyte-derived human dendritic cells were plated in 96 well U bottom plate, with 100 μl antibodies. The cells were incubated in a humidified 37° C., 5% $CO_2$ incubator and supernatants were collected after three days. Human IFN-γ ELISA was done on the supernatants using a R&D ELISA kit (# SIF50).

In experiments performed essentially as described in this assay, 4 nM of Antibody C increased IFN-γ levels by approximately three-fold while 8 nM of Antibody C increased IFN-γ levels by approximately five-fold. These results demonstrate the ability of Antibody C to enhance allogeneic T-cell response in this assay.

In Vivo Functional Studies

1. Antibody C in HCC827 Human NSCLC Xenograft Model

The efficacy of the antibodies of the present invention can be tested in the HCC827 human NSCLC xenograft model to assess the ability to delay or destroy established tumors in the model through enhancement of T-cell response to allo-antigens.

For the study, on day 0, NSG mice from Jackson Laboratories (7 weeks of age, female, in groups of 8 mice) were implanted into the flank subcutaneously with 10×106 HCC827 cells in HBSS (0.2 ml total volume). Bulk human T-cells isolated from whole blood (New York Blood Center) were expanded using Human T-Activator CD3/CD28 Dynabeads® for 10 days and cryopreserved. T-cells were thawed, washed, counted, and infused intravenously (2.5×106 T-cells in 0.2 ml PBS per mouse) into HCC827 tumor-bearing mice on day 36. Starting on day 36, mice were treated with an i.p. injection of human IgG (20 mg/kg), the parental anti-PD-L1 antibody of Antibody C (10 mg/kg) in combination with the parental anti-TIM-3 antibody of Antibody B (10 mg/kg) or the parental anti-TIM-3 antibody of Antibody C (10 mg/kg), Antibody B (20 mg/kg) or Antibody C (20 mg/kg), once weekly for three weeks (dosed on d36, d43, d50). Animal well-being and behavior, including grooming and ambulation were monitored at least twice per week. Body weight and tumor volume were measured twice a week. Tumor volumes were measured twice per week starting on day 4 post cell implantation using electronic calipers as described in the SOP entitled: IM-Tumor Growth Measurement. Tumor volume was calculated using a formula: Tumor Volume (mm3)=$\pi/6$*Length*Width$^2$.

In experiments performed essentially as described in this assay, at day 50, the combination of the parental anti-PD-L1 antibody of Antibody C and the parental anti-TIM-3 antibody of Antibody C slowed tumor growth by 62.5% when comparing tumor size for treated versus untreated (T/C=27.5%). The combination of the parental anti-PD-L1 antibody of Antibody B and the parental anti-TIM-3 antibody of Antibody B slowed tumor growth with T/C=41.5%. At day 50, Antibody C treatment caused the tumor size to regress 8.3% compared to day 35 when the T-cells were infused. Therefore, while the combination of a TIM-3 antibody and a PD-L1 antibody in the HCC827 model slowed tumor growth, Antibody C led to regression of tumor size.

2. Antibody C in L55 Tumor Bearing Humanized HSCTFL-NOG-F Mice (NSCLC Model)

The efficacy of the antibodies of the present invention can be tested in the L55 human NSCLC xenograft model to assess the ability to delay or destroy established tumors in the model through enhancement of T-cell response to allo-antigens.

Female NOG mice from Jackson Laboratories were engrafted with Human CD34$^+$ hematopoietic stem cell. The presence of huCD45$^+$ cells and murine CD45$^+$ cells (mCD45) in the mouse peripheral blood was confirmed by flow cytometry 16 weeks post-engraftment. For the study, on day 0, HSCTFL-NOG-F mice were implanted into the flank subcutaneously with L55 fragment. L55 cells were cultured in RPMI-1640 Medium with 10% fetal bovine serum plus 1 mM Na Pyruvate and L-Glutamine and L55 tumors were grown on NSG mice to produce fragment for this study. Animals were randomized on an average tumor volume of approximately 180 mm3 into groups. Treatment was initiated on day 26 followed by a weekly administration (Q7DX3) of all antibodies on days 33, and 40. For the combination of the parental anti-PD-L1 antibody of Antibody C and the parental anti-TIM-3 antibody of Antibody C, each antibody was dosed at 10 mg/kg. For the bispecific antibody, Antibody C was dosed at 20 mg/kg. Animal well-being and behavior, including grooming and ambulation were monitored at least twice per week. Body weight and tumor volume were measured twice a week. Tumor volumes were measured twice per week starting on day 4 post cell implantation using electronic calipers as described in the SOP entitled: IM-Tumor Growth Measurement. Tumor volume was calculated using a formula: Tumor Volume (mm$^3$)=$\pi/6$*Length*Width$^2$.

In experiments performed essentially as described in this assay, at day 40, the combination of the parental anti-PD-L1 antibody of Antibody C and the parental anti-TIM-3 antibody of Antibody C had a T/C % of 50% when comparing tumor size for treated versus control (P=0.314 for tumor volume). At day 40, Antibody C treatment delayed tumor growth compared to combination of the two parental antibodies and had a T/C % of 7% when comparing tumor size for treated versus control (P=0.013 for tumor volume).

3. Combination Therapy of Antibody C and Pemetrexed in L55 Human NSCLC Xenograft Model The efficacy of the antibodies of the present invention in combination with pemetrexed can be tested in the L55 human NSCLC xenograft model to assess the ability to delay or destroy established tumors in the model through enhancement of T-cell response to allo-antigens.

L55 cells will be cultured in RPMI-1640 Medium with 10% fetal bovine serum plus 1 mM Na Pyruvate and L-Glutamine. For the study, on day 0, NSG mice from Jackson Laboratories (7 weeks of age, female, in groups of 8 mice) were implanted into the flank subcutaneously with 5×106 L55 cells in (50/50) matrigel:HBSS (0.2 ml total volume). Bulk human PBMC were isolated from apheresis (BioSpec) and infused intravenously (11×10$^6$ PBMC cells in 0.2 ml PBS per mouse) into L55 tumor-bearing mice on day 33 when the tumors reach ~250 mm3. Starting on day 34, mice were treated with an i.p. injection of human IgG (20 mg/kg), Antibody C (20 mg/kg), or in combination with pemetrexed (50 mg/kg). Pemetrexed was doing 5 days every week with 2 days break in between. Antibody was doing once weekly for four weeks (dosed on d34, d41, d48, d55). On day 47, a second batch of 5M PBMCs (same lot as first infusion) were injected into L55 tumor-bearing mice. Animal well-being and behavior, including grooming and ambulation were monitored at least twice per week. Body weight and tumor volume were measured twice a week. Tumor volumes were measured twice per week starting on day 4 post cell implantation using electronic calipers as described in the SOP entitled: IM-Tumor Growth Measurement. Tumor volume was calculated using a formula: Tumor Volume (mm$^3$)=$\pi/6$*Length*Width$^2$.

In experiments performed essentially as described in this assay, Antibody C itself or the combination of huIgG and pemetrexed resulted in "No Effect" as defined by the Bliss Independence method in this model. The combination of Antibody C and pemetrexed slowed tumor growth with T/C=48.9% at the end of study.

In Vitro Cytokine Release Study with Plate-Bound Antibody C in Human PBMCs

The potential for antibodies of the present invention to elicit cytokine release syndrome can be assessed by measuring cytokine release in a plate bound assay using fresh peripheral blood mononuclear cells (PBMCs). Cytokine release syndrome induced by the treatment with antibodies is an undesirable reaction for most patients, and treatment with a bispecific antibody could elevate the risk.

Freshly isolated PBMCs from six healthy subjects were incubated with plate bound Antibody C, or control antibodies for 24 hours, over a broad titration range from 0.1 μg to 10 μg. Positive controls were anti-human CD3ε antibody, OKT3, and a homolog of CD28-specific superagonist therapeutic antibody, TGN1412. Both antibodies are known to cause a cytokine storm in the clinic. The negative control was an effector null hIgG1 (IgG1-EN) isotype antibody. A total of 2×10$^5$ cells per well (200 μL) were added in triplicates to the antibody-coated plates and incubated for 24 hours at 37° C., 5% CO2. Following incubation, plates were centrifuged at 400 g for 5 minutes; cell culture supernatants were collected and stored at −80° C. before cytokine determination. Using a custom 5-plex assay MSD kit (Cat# K151A0H-2; Meso Scale Discovery), five cytokines including, IFN-γ, IL-2, IL-6, IL-10, and TNF-α were measured in cell culture supernatants following manufacturer instructions.

In experiments performed essentially as described in this assay, incubation of human PBMCs with Antibody C over a broad range of concentrations did not result in significant levels of cytokine release for IFN-γ, IL-2, IL-6, IL-10, and TNF-α. In contrast, incubation of PBMCs with anti-CD38 and TGN1412 positive control antibodies resulted in robust cytokine production for all five cytokines analyzed in most donors.

In Vitro Cytokine Release Study with Soluble Antibody C in Human Whole Blood

The potential for antibodies of the present invention to elicit cytokine release syndrome can also be assessed by measuring cytokine release with soluble antibodies of the present invention in human whole blood.

Fresh human whole blood samples from 10 healthy donors were incubated with soluble Antibody C, or control antibody for 24 hours, at 100 μg/mL. Positive controls included anti-human CD3ε antibody, OKT3, and a homolog anti-human CD52 (Campath). OKT3 and Campath are known to cause 'cytokine storm' in the clinic. The negative controls were a commercially available therapeutic antibody infliximab not associated with cytokine release syndrome in clinic and an effector null (EN) hIgG1 (IgG1-EN) isotype antibody. A broad panel of cytokines including, IFN-γ, IL-1β, IL-2, IL-4, IL-6, IL-8, IL-10, IL-12p70, IL-13, and TNF-α was analyzed using a custom multiplex assay based on the Mesoscale platform in human plasma supernatants (Cat#K15049D-1, Meso Scale Discovery).

In experiments performed essentially as described in this assay, incubation of human blood samples with Campath or OKT3 resulted in robust cytokine release in all donors of several of the cytokines analyzed including the cytokines associated with CRS (IFN-γ, IL-6, TNF-α, and IL-10). In contrast, incubation with Antibody C or with infliximab did not trigger any significant cytokine release in 10 healthy donors. Antibody C did not result in robust cytokine release when incubated with human whole blood for up to 24 hours at concentration up to 100 μg/ml.

In Vitro Immunogenicity Assay

Antibodies of the present invention are engineered to be heterodimeric with each half of the antibody binding a different target. With the non-natural makeup of the heterodimeric antibodies, immunogenicity is a potential risk that must be assessed.

The EpiScreen™ DC: T-cell assay was used to determine the relative potential for clinical immunogenicity of Antibody C. Monocyte-derived dendritic cells were prepared from the PBMCs of a cohort of 50 healthy donors, loaded with Antibody C, and induced to a mature phenotype in order to present T-cell epitopes to autologous purified CD4+ T-cells. T-cell responses were measured using T-cell proliferation ([$^3$H]-Thymidine uptake) and IL-2 cytokine secretion (ELISpot).

EpiScreen™ time course T-cell assays with a group of known biologics (such as infliximab, adalimumab, and bevacizumab) have shown a clear correlation between the frequency of donor T-cell responses in the EpiScreen™ assay and the level of immunogenicity (anti-protein therapeutic antibody responses) observed in the clinic. High frequency donor responses have been observed in EpiScreen™ assays for immunogenic antibodies such as alemtuzumab, whereas relatively low frequency donor responses were observed for non-immunogenic antibodies such as omalizumab and trastuzumab. In general, protein therapeutics that induce less than or equal to a 10% positive response in the EpiScreen™ assay are associated with a low risk of immunogenicity in the clinic.

In experiments performed essentially as described in this assay, analysis of the frequency and magnitude of the CD4+ T-cell responses indicated Antibody C induced modest positive responses in 6-8% of the donor cohort and therefore show a low risk of clinical immunogenicity.

In Vitro Analysis of Antibody C Immune Effector Function

As a potential therapy in cancer with a bispecific antibody towards human PD-L1 and human TIM-3, immune effector function produced by the antibody is not desirable. Antibody C is engineered to lack immune effector function. In order to confirm the absence of immune effector function, Antibody C was tested in standard solid phase binding assays for binding to human Fcγ receptors and C1q, and for induction of an antibody-dependent cellular cytotoxicity (ADCC), antibody-dependent cellular phagocytosis (ADCP) and complement-dependent cytotoxicity (CDC) response in standard cell-based in vitro assays.

For the solid-phase human Fcγ receptor binding assay, recombinant Fcγ receptor (FcγR) proteins used in this assay are FcγRI, FcγRIIa, FcγRIIb, and FcγRIIIa(V). Receptor protein was diluted in PBS and coated (50 ng/well) onto a Meso Scale plate (MSD cat# L15XA-3). After an overnight incubation at 4° C., plates were washed with PBS/0.05% Tween-20 (PBST) three times and blocked for 1-2 hours at room temperature with 150 μL/well of 5% MSD Blocker A (MSD cat# R93BA-1) in PBST. The plates were then washed three times with PBST and 30 μL of test antibody or control antibody (Table 3), diluted in 1% MSD Blocker A, was added to each well and allowed to incubate for two hours. Following the incubation, the plates were washed two times with PBST and 30 μL of secondary antibody (MSD Cat#D20TF-6) was added to each well and allowed to incubate for one hour at room temperature with agitation. The plates were then washed with PBST and 150 μL of a 1× Read Buffer (MSD cat # R92TC-1) was added to each well. The plates were then read on the Sector Imager 2400.

For the C1q binding ELISA assay, a 96-well polystyrene ELISA plate (Thermo Scientific Cat. 3855) was coated with test antibodies and controls (Rituximab-IgG1-effector null and another human IgG1-effector null antibody) at concentrations ranging from 200-0.0305 μg/mL in PBS. After an overnight incubation at 4° C., the plates were washed three times with PBST and then blocked with 300 μl of casein buffer (Thermo Fisher cat#37528) for two hours at room temperature. The plates were washed 3 times with PBST and then 0.5 μg/well of C1q (Quidel Cat# A400), diluted in casein blocking buffer, was added. After two hours at room temperature, the plates were washed three times with PBST and 50 μL of secondary antibody (1:200, Abd Serotec Inc #2221-5004P) was added to each well. The plates were incubated for one hour at room temperature and then washed three times with PBST. 100 μL of 3,3',5,5'-Tetramethylbenzidine (TMB: KPL cat#50-65-01/02), a substrate of HRP, was then added to each well and the plates were incubated at room temperature for 20 minutes. The reaction was stopped (KPL cat#50-85-06) and the absorbance was measured at 450 nM using a microplate reader.

For the ADCC assay, PD-L1 and TIM-3-positive target cells and CD20-positive Wil2S cells were seeded in 96-well flat-bottom plates (Perkin Elmer, #600-5680) at a density of 10000 cell/well in 50 μL of ADCC assay buffer (0.5% BSA in RPMI 1640). The cells were incubated for 30 minutes (all incubations with cells were performed at 37° C. and 5% $CO_2$ unless otherwise stated) followed by the addition of 25

μL/well of titrated test antibodies diluted in ADCC assay buffer. Following a 30 minute incubation with test antibodies, 25 μL of effector cells (FcγRIIIa-positive Jurkat cells with NFAT-luciferase reporter construct) were added at a ratio of 15:1 (effector:target) and incubated for 5-6 hours. Luciferase activity of activated effector cells was measured after a 10 minute room temperature incubation with 100 μL of Bright-Glo™ Luciferase substrate (Promega, #G7940). Luminescence was quantified using a microtiter plate reader and data were analyzed using a four-parameter model to determine $EC_{50}$ values for each antibody.

For the ADCP assay, PD-L1 and TIM-3-positive target cells and CD20-positive Wil2S cells were seeded in 96-well flat-bottom plates (Perkin Elmer, #600-5680) at a density of 10000 cell/well in 50 μL of ADCP assay buffer (0.5% BSA in RPMI 1640). The cells were incubated for 30 minutes (all incubations with cells were performed at 37° C. and 5% $CO_2$ unless otherwise stated) followed by the addition of 25 μL/well of titrated test antibodies diluted in ADCP assay buffer. Following a 30 minute incubation with test antibodies, 25 μL of effector cells (FcγRIIa-positive Jurkat cells with NFAT-luciferase reporter construct; Promega G9885) were added at a ratio of 6:1 (effector:target) and incubated for 5-6 hours. Luciferase activity of activated effector cells was measured after a 10 minute room temperature incubation with 100 μL of Bright-Glo™ Luciferase substrate (Promega, #G7940). Luminescence was quantified using a microtiter plate reader and data were analyzed using a four-parameter model to determine $EC_{50}$ values for each antibody.

For the CDC assay, adherent target cells were seeded in 96-well white flat-bottom plates (Perkin Elmer, #600-5680) at 25000 cells/well in 100 μL/well of cell growth medium. After an overnight incubation (all incubations with cells were performed at 37° C. and 5% $CO_2$ unless otherwise stated) the medium was removed and 50 μl CDC assay buffer (RPMI 1640, 10% FBS with 0.1% BSA, and 25 mM HEPES) was added. Suspension cells were seeded on the day of the assay at a density of 50,000 cell/well in 50 μL of CDC assay buffer. Test and control antibodies were added in duplicate to the plates and incubated for 30 minutes. Following the incubation, 50 μL of human complement (S1764; Sigma), diluted in 5-mL of assay buffer (1:5), was then added to each well for one hour. Following the incubation, 16 μL/well of Alamar Blue reagent (Invitrogen, DAL1100) was added to each well. Plates were incubated for 22 hours and then removed from the incubator and allowed equilibrate to room temperature for 5 minutes. Fluorescence was read on Synergy Neo2 (excitation:560 nm, emission: 590 nm) and CDC cell lysis was expressed relative to complete cell lysis induced by Triton X 100.

In experiments performed essentially as described in this assay, Antibody C demonstrated no specific binding of to any of the tested human Fcγ receptors, nor to C1q. Furthermore, there was no detectable response in cell-based ADCC, ADCP or CDC assays using relevant TIM-3 and PD-L1 positive cell lines for Antibody C. These results demonstrate Antibody C lacks detectable immune effector function within the limits of detection of the assays performed.

Pharmacokinetics in Monkey

Antibodies of the present invention can be tested for stability in monkeys using serum pharmacokinetic (PK) analysis in ELISA assays.

To characterize the serum PK of Antibody C, serum samples were analyzed in three different enzyme-linked immunosorbent assay (ELISA) formats. A total Immunoglobulin (IgG) ELISA was employed to quantitate presence of total IgG backbone regardless of binding competency to TIM-3 or PD-L1. Standard curve range for Antibody C was 125-8000 ng/mL, with an upper limit of quantitation (ULOQ) of 3000 ng/mL and a lower limit of quantitation (LLOQ) of 300 ng/mL. In addition, a TIM-3 antigen capture ELISA and a PD-L1 antigen capture ELISA were employed to quantitate presence of active drug in serum. For the TIM-3 antigen capture ELISA, the assay range for Antibody C was 125-8000 ng/mL, with a ULOQ of 3000 ng/mL and a LLOQ of 300 ng/mL. For the PD-L1 antigen capture ELISA, the standard curve range for Antibody C was 125-8000 ng/mL, with an upper limit of quantitation (ULOQ) of 3000 ng/mL and a lower limit of quantitation (LLOQ) of 300 ng/mL.

In experiments performed essentially as described in this assay, total IgG and functional antigen capture ELISA assays for TIM-3 and PD-L1 were quantitatively similar at all dose levels, indicating stability in Antibody C and retention of functional binding capacity over time in vivo.

Amino Acid and Nucleotide Sequences

SEQ ID NO: 1 (human PD-L1)
MRIFAVFIFMTYWHLLNAFTVTVPKDLYVVEYGSNMTIECKFPVEKQLDLAALIVYWEMEDKNIIQFVHGEEDLKV
QHSSYRQRARLLKDQLSLGNAALQITDVKLQDAGVYRCMISYGGADYKRITVKVNAPYNKINQRILVVDPVTSEHE
LTCQAEGYPKAEVIWTSSDHQVLSGKTTTTNSKREEKLFNVTSTLRINTTTNEIFYCTFRRLDPEENHTAELVIPE
LPLAHPPNERTHLVILGAILLCLGVALTFIFRLRKGRMMDVKKCGIQDTNSKKQSDTHLEET SEQ ID NO: 2 (human TIM-3)
MFSHLPFDCVLLLLLLLLTRSSEVEYRAEVGQNAYLPCFYTPAAPGNLVPVCWGKGACPVFECGNVVLRTDERDVN
YWTSRYWLNGDFRKGDVSLTIENVTLADSGIYCCRIQIPGIMNDEKFNLKLVIK SEQ ID NO: 3 (HCVR of PD-L1 Ab in Antibody A, Antibody B, and Antibody C)
QVQLVQSGAEVKKPGSSVKVSCKASGGTFSSYAISWVRQAPGQGLEWMGGIIPIFGTANYAQKFQGRVTITADKST
STAYMELSSLRSEDTAVYYCARSPDYSPYYYYGMDVWGQGTTVTVSS SEQ ID NO: 4 (LCVR of PD-L1 Ab in Antibody A, Antibody B, and Antibody C)
QSVLTQPPSASGTPGQRVTISCSGSSSNIGSNTVNWYQQLPGTAPKLLIYGNSNRPSGVPDRFSGSKSGTSASLAI
SGLQSEDEADYYCQSYDSSLSGSVFGGGIKLTVLG SEQ ID NO: 5 (HCVR of TIM-3 Ab in Antibody A)
EVQLLESGGGLVQPGGSLRLSCAASGFTFSSYYMSWVRQAPGKGLEWVSAISGSGGSTYYADSVKGRFTISRDNSK
NTLYLQMNSLRAEDTAVYYCARYARTAFDLWGQGTLVTVSS SEQ ID NO: 6 (HCVR of TIM-3 Ab in Antibody B)
EVQLLESGGGLVQPGGSLRLSCAASGFSFSSFYFSWVRQAPGKGLEWVSAISGNGRSTYYADSVKGRFTISRDNSK
NTLYLQMNSLRAEDTAVYYCARYYNTGFDLWGQGTLVTVSS

| Amino Acid and Nucleotide Sequences |
| --- |

SEQ ID NO: 7 (HCVR of TIM-3 Ab in Antibody C)
EVQLLESGGGLVQPGGSLRLSCAASGFTFSSYYMSWVRQAPGKGLEWVSAISGNGKSTYYADSVKGRFTISRDNSK
NTLYLQMNSLRAEDTAVYYCARYYNTGFDLWGQGTLVTVSS SEQ ID NO: 8 (LCVR of TIM-3 Ab in Antibody A)
DIVMTQSPSSLSASVGDRVTITCQASEAIYGYLNWYQQKPGKAPKLLIYAASSLPIGVPSRFSGSGSGTDFTLTIS
SLQPEDFATYYCQQAYGFPPTFGQGTKLEIK SEQ ID NO: 9 (LCVR of TIM-3 Ab in Antibody B)
DIVMTQSPSSLSASVGDRVTITCQASEAIYGYLNWYQQKPGKAPKLLIYAASSLPIGVPSRFSGSGSGTDFTLTIS
SLQPEDFATYYCQQAYGFPPTFGQGTKLEIK SEQ ID NO: 10 (LCVR of TIM-3 Ab in Antibody C)
DIVMTQSPSSLSASVGDGVTITCQASQDIYNYLNWYQQKPGKAPKLLIYYASSIVSGVPSRFSGSGSGTDFTLTIS
SLQPEDFATYYCQQASSFPPTFGQGTKLEIK SEQ ID NO: 11 (HC of PD-L1 Ab in Antibody A, Antibody B, and Antibody C)
QVQLVQSGAEVKKPGSSVKVSCKASGGTFSSYAISWVRQAPGQGLEWMGGIIPIFGTANYAQKFQGRVTITADKST
STAYMELSSLRSEDTAVYYCARSPDYSPYYYYGMDVWGQGTTVTVSSASTKGPSVFPLAPSSKSTSGGTAALGCLV
KDYFPEPVTVSWNSGALTSGVHTFPAVLQSSGLYSLKSVVTVPSSSLGTQTYICNVNHKPSNTKVDKRVEPKSCDK
THTCPPCPAPEAAGGPSVFLFPPKPKDTLMISRTPEVTCVVVSVSHEDPEVKFNWYVDGVEVHNAKTKPREEQYNS
TYRVVSVLTVLHQDWLNGKEYKCKVSNKALPAPIEKTISKAKGQPREPQVYVLPPSRDELTKNQVSLLCLVKGFYP
SDIAVEWESNGQPENNYLTWPPVLDSDGSFFLYSKLTVDKSRWQQGNVFSCSVMHEALHNHYTQKSLSLSPGK SEQ ID NO: 12 (LC of PD-L1 Ab in Antibody A, Antibody B, and Antibody C)
QSVLTQPPSASGTPGQRVTISCSGSSSNIGSNTVNWYQQLPGTAPKLLIYGNSNRPSGVPDRFSGSKSGTSASLAI
SGLQSEDEADYYCQSYDSSLSGSVFGGGIKLTVLGQPKAAPSVTLFPPSSEELQANKATLVCLISDFYPGAVTVAW
KADSSPVKAGVETTTPSKQSNNKYAAESELSLTPEQWKSHRSYSCQVTHEGSTVEKTVAPAECS SEQ ID NO: 13 (HC of TIM-3 Ab in Antibody A)
EVQLLESGGGLVQPGGSLRLSCAASGFTFSSYYMSWVRQAPGKGLEWVSAISGSGGSTYYADSVKGRFTISRDNSK
NTLYLQMNSLRAEDTAVYYCARYARTAFDLWGQGTLVTVSSASTKGPSVFPEAPSSKSTSGGTAALGCLVTDYFPE
PVTVSWNSGALTSGVHTFPAVLESSGLYSLWSVVTVPSSSLGTQTYICNVNHKPSNTKVDKRVEPKSCDKTHTCPP
CPAPEAAGGPSVFLFPPKPKDTLMISRTPEVTCVVVSVSHEDPEVKFNWYVDGVEVHNAKTKPREEQYNSTYRVVS
VLTVLHQDWLNGKEYKCKVSNKALPAPIEKTISKAKGQPREPQVYVYPPSRDELTKNQVSLTCLVKGFYPSDIAVE
WESNGQPENNYKTTPPVLDSDGSFALVSKLTVDKSRWQQGNVFSCSVMHEALHNHYTQKSLSLSPGK SEQ ID NO: 14 (HC of TIM-3 Ab in Antibody B)
EVQLLESGGGLVQPGGSLRLSCAASGFSFSSFYFSWVRQAPGKGLEWVSAISGNGRSTYYADSVKGRFTISRDNSK
NTLYLQMNSLRAEDTAVYYCARYYNTGFDLWGQGTLVTVSSASTKGPSVFPEAPSSKSTSGGTAALGCLVTDYFPE
PVTVSWNSGALTSGVHTFPAVLESSGLYSLWSVVTVPSSSLGTQTYICNVNHKPSNTKVDKRVEPKSCDKTHTCPP
CPAPEAAGGPSVFLFPPKPKDTLMISRTPEVTCVVVSVSHEDPEVKFNWYVDGVEVHNAKTKPREEQYNSTYRVVS
VLTVLHQDWLNGKEYKCKVSNKALPAPIEKTISKAKGQPREPQVYVYPPSRDELTKNQVSLTCLVKGFYPSDIAVE
WESNGQPENNYKTTPPVLDSDGSFALVSKLTVDKSRWQQGNVFSCSVMHEALHNHYTQKSLSLSPGK SEQ ID NO: 15 (HC of TIM-3 Ab in Antibody C)
EVQLLESGGGLVQPGGSLRLSCAASGFTFSSYYMSWVRQAPGKGLEWVSAISGNGKSTYYADSVKGRFTISRDNSK
NTLYLQMNSLRAEDTAVYYCARYYNTGFDLWGQGTLVTVSSASTKGPSVFPEAPSSKSTSGGTAALGCLVTDYFPE
PVTVSWNSGALTSGVHTFPAVLESSGLYSLWSVVTVPSSSLGTQTYICNVNHKPSNTKVDKRVEPKSCDKTHTCPP
CPAPEAAGGPSVFLFPPKPKDTLMISRTPEVTCVVVSVSHEDPEVKFNWYVDGVEVHNAKTKPREEQYNSTYRVVS
VLTVLHQDWLNGKEYKCKVSNKALPAPIEKTISKAKGQPREPQVYVYPPSRDELTKNQVSLTCLVKGFYPSDIAVE
WESNGQPENNYKTTPPVLDSDGSFALVSKLTVDKSRWQQGNVFSCSVMHEALHNHYTQKSLSLSPGK SEQ ID NO: 16 (LC of TIM-3 Ab in Antibody A)
DIVMTQSPSSLSASVGDGVTITCQASQDIYNYLNWYQQKPGKAPKLLIYAASSLQSGVPSRFSGSGSGTDFTLTIS
SLQPEDFATYYCQQANSFPPTFGQGTKLEIKRTVAAPSVFIFPPSDEQLKSGTARVGCLLNNFYPREAKVQWKVDN
ALQSGNSQESVTEQDSKDSTYSLRSALTLSKADYEKHKVYACEVTHQGLSSPVTKSFNRGEC SEQ ID NO: 17 (LC of TIM-3 Ab in Antibody B)
DIVMTQSPSSLSASVGDRVTITCQASEAIYGYLNWYQQKPGKAPKLLIYAASSLPIGVPSRFSGSGSGTDFTLTIS
SLQPEDFATYYCQQAYGFPPTFGQGTKLEIKRTVAAPSVFIFPPSDEQLKSGTARVGCLLNNFYPREAKVQWKVDN
ALQSGNSQESVTEQDSKDSTYSLRSALTLSKADYEKHKVYACEVTHQGLSSPVTKSFNRGEC SEQ ID NO: 18 (LC of TIM-3 Ab in Antibody C)
DIVMTQSPSSLSASVGDGVTITCQASQDIYNYLNWYQQKPGKAPKLLIYYASSIVSGVPSRFSGSGSGTDFTLTIS
SLQPEDFATYYCQQASSFPPTFGQGTKLEIKRTVAAPSVFIFPPSDEQLKSGTARVGCLLNNFYPREAKVQWKVDN
ALQSGNSQESVTEQDSKDSTYSLRSALTLSKADYEKHKVYACEVTHQGLSSPVTKSFNRGEC SEQ ID NO: 19 (region from CH1 domain of PD-L1 Ab HC)
GPSVFPLAPSSKSTSGGTAALGCLVKDYFPEPVTVSWNSGALTSGVHTFPAVLQSSGLYSLKS SEQ ID NO: 20 (region from CH2 domain of PD-L1 Ab HC)
APEAAGGPSVFLFPPKPKDTLMISRTPEVTCVVVS SEQ ID NO: 21 (region from CH2 domain of PD-L1 Ab HC)
SNKALPAPIEK -continued Amino Acid and Nucleotide Sequences SEQ ID NO: 22 (region from CH3 domain of PD-L1 Ab HC)
REPQVYVLPPSRDELTKNQVSLLCLVKGFYPSDIAVEWESNGQPENNYLTWPPVLDSDGSF SEQ ID NO: 23 (region from CH1 domain of TIM-3 Ab HC)
EAPSSKSTSGGTAALGCLVTDYFPEPVTVSWNSGALTSGVHTFPAVLESSGLYSLWSVVTVPS SEQ ID NO: 24 (region from CH2 domain of TIM-3 Ab HC)
APEAAGGPSVFLFPPKPKDTLMISRTPEVTCVVVS SEQ ID NO: 25 (region from CH2 domain of TIM-3 Ab HC)
APIEKTISKAK SEQ ID NO: 26 (region from CH3 domain of TIM-3 Ab HC)
VYPPSRDELTKNQVSLTCLVKGFYPSDIAVEWESNGQPENNYKTTPPVLDSDGSFALVSKL SEQ ID NO: 27 (region from light chain constant region of PD-L1 Ab)
ANKATLVCLISDFYPGAVTVAWKADSSPVKAGVETTTPSKQSNNKYAAESE SEQ ID NO: 28 (region from light chain constant region of TIM-3 Ab)
RVGCLLNNFYPREAKVQWKVDNALQSGNSQESVTEQDSKDSTYSLRSALTL SEQ ID NO: 29 DNA Sequence of PD-L1 LC for Antibody C
CAGTCCGTCC TGACTCAGCC ACCTTCCGCT AGCGGTACCC CCGGCCAGAG AGTGACAATC TCATGCTCCG
GTTCCAGCTC TAACATTGGC TCTAACACTG TCAATTGGTA CCAGCAGCTG CCAGGAACCG CACCAAAGCT
GCTGATCTAT GGAAACTCAA ATAGGCCTAG CGGGGTGCCA GACCGGTTTA GCGGATCTAA AGTGGGACT
TCAGCTTCCC TGGCAATTTC TGGACTGCAG AGTGAGGACG AAGCTGATTA CTATTGCCAG TCCTACGATA
GTTCACTGAG CGGTTCCGTG TTCGGCGGAG GGATCAAGCT GACAGTCCTG GGCCAGCCCA AGGTGAGTTC
TAGAGGATCC ATCTGGGATA AGCATGCTGT TTTCTGTCTG TCCCTAACAT GCCCTGTGAT TATCCGCAAA
CAACACACCC AAGGGCAGAA CTTTGTTACT TAAACACCAT CCTGTTTGCT TCTTTCCTCA GGCCGCTCCT
TCCGTGACTC TGTTTCCCCC TTCCAGCGAG GAACTGCAGG CCAATAAGGC CACCCTGGTG TGCCTGATTA
GCGACTTCTA TCCTGGAGCT GTGACAGTCG CATGGAAGGC CGATTCTAGT CCAGTGAAAG CAGGGGTCGA
GACCACAACT CCCTCCAAGC AGAGCAACAA CAAGTACGCA GCCGAGTCTG AACTGAGTCT GACCCCAGAA
CAGTGGAAGT CCCACAGGAG TTATTCATGC CAGGTGACCC ATGAGGGCTC CACAGTGGAG AAGACCGTGG
CCCCTGCTGA GTGTAGC SEQ ID NO: 30 DNA Sequence of TIM-3 LC for Antibody C
GACATCGTGA TGACCCAGTC CCCTTCCAGC CTGTCTGCCT CCGTGGGCGA CGGAGTGACC ATCACATGCC
AGGCTAGCCA GGATATCTAC AACTATCTGA ATTGGTACCA GCAGAAGCCT GGCAAGGCCC AAAGCTGCT
GATCTATTAC GCTTCTTCCA TCGTGTCTGG AGTGCCATCC AGGTTCAGCG GATCTGGATC CGGAACCGAC
TTTACCCTGA CAATCAGCTC TCTGCAGCCT GAGGATTTCG CCACATACTA TTGCCAGCAG GCTTCCTCTT
TCCCCCCTAC CTTTGGCCAG GGCACAAAGC TGGAGATCAA GAGAACCGTG GCCGCTCCA CCGTGTTCAT
CTTTCCACCC AGCGACGAGC AGCTGAAGTC TGGCACAGCT AGGGTGGGCT GTCTGCTGAA CAACTTCTAC
CCCCGGGAGG CCAAGGTGCA GTGGAAGGTG GATAACGCTC TGCAGAGCGG CAATTCTCAG GAGTCCGTGA
CCGAGCAGGA CAGCAAGGAT TCTACATATT CCCTGAGAAG CGCCCTGACA CTGAGCAAGG CCGATTACGA
GAAGCACAAG GTGTATGCTT GCGAGGTGAC CCATCAGGGC CTGTCCAGCC CAGTGACAAA GTCTTTCAAT
CGCGGCGAGT GT SEQ ID NO: 31 DNA Sequence of PD-L1 HC for Antibody C
CAGGTCCAGC TGGTGCAGAG CGGAGCCGAA GTGAAGAAAC CCGGTAGCAG CGTCAAAGTG TCATGTAAAG
CCTCAGGGGG AACATTCTCC AGCTACGCCA TCTCCTGGGT GAGACAGGCT CCAGGACAGG GACTGGAGTG
GATGGGAGGA ATCATCCCTA TCTTCGGCAC CGCCAACTAC GCTCAGAAGT TCAGGGCCG CGTGACCATC
ACAGCCGACA AGAGCACCTC TACAGCTTAT ATGGAGCTGT CTTCCCTGAG AAGCGAGGAT ACAGCCGTGT
ACTATTGCGC TCGCTCCCCC GACTACAGCC CTTACTATTA CTATGGCATG GACGTGTGG GCCAGGGCAC
CACAGTGACC GTGAGCTCTG CTAGCACAAA GGGCCCATCC GTGTTCCCAC TGGCTCCATC CAGCAAGTCC
ACCAGCGGAG GAACAGCCGC TCTGGGCTGT CTGGTAAGG ACTATTTCCC AGAGCCAGTG ACCGTGTCCT
GGAACAGCGG CGCCCTGACC TCTGGAGTGC ACACATTTCC CGCTGTGCTG CAGTCTTCCG GCCTGTACTC
TCTGAAGTCC GTGGTGACCG TGCCTAGCTC TTCCCTGGGC ACCCAGACAT ATATCTGCAA CGTGAATCAC
AAGCCTTCCA ATACAAAGGT GGACAAGAGG GTGGAGCCAA AGAGCTGTGA TAAGACCCAT ACATGCCCCC
CTTGTCCTGC TCCAGAGGCT GCTGGAGGAC CAAGCGTGTT CCTGTTTCCA CCCAAGCCCA AGGACACCCT
GATGATCTCT AGGACCCCTG AGGTGACATG CGTGGTGGTG TCCGGTGTCC ACGAGGACCC AGAGGTGAAG
TTTAACTGGT ACGTGGATGG CGTGGAGGTG CATAATGCTA AGACCAAGCC TAGGGAGGAG CAGTACAACA
GCACCTATCG GGTGGTGTCT GTGCTGACAG TGCTGCATCA GGATTGGCTG AACGGCAAGG AGTATAAGTG
CAAGGTGTCT AATAAGGCCC TGCCCGCTCC TATCGAGAAG ACCATCTCCA AGGCCAAGGG CCAGCCTAGG
GAGCCACAGG TGTACGTGCT GCCTCCAAGC CGGGACGAGC TGACAAAGAA CCAGGTGTCT CTGCTGTGCC
TGGTGAAGGG CTTCTATCCA TCTGATATCG CTGTGGAGTG GGAGTCCAAT GGCCAGCCCG AGAACAATTA
CCTGACCTGG CCCCCTGTGC TGGACAGCGA TGGCTCTTTC TTTCTGTATT CCAAGCTGAC AGTGGATAAG
AGCCGGTGGC AGCAGGGCAA CGTGTTCTCC TGTTCTGTGA TGCACGAGGC ACTGCACAAT CATTACACCC
AGAAATCCCT GTCACTGAGC CCCGGCAAG SEQ ID NO: 32 DNA Sequence of TIM-3 HC for Antibody C
GAGGTGCAGC TGCTGGAGTC TGGGGGGGGT CTGGTGCAGC CCGGGGGTAG CCTGCGTCTG TCTTGTGCCG
CCTCTGGGTT TACTTTTTCC AGCTACTATA TGAGCTGGGT GAGACAGGCT CCTGGCAAGG GCCTGGAGTG
GGTGTCTGCC ATCAGCGGCA ACGGCAAATC TACCTACTAT GCTGACTCCG TGAAGGGCAG ATTCACCATC
AGCCGCGATA ACTCTAAGAA TACACTGTAC CTGCAGATGA ACAGCCTGCG CGCTGAGGAC ACCGCCGTGT
ACTATTGCGC CAGATATTAT AACACAGGCT TCGATCTGTG GGGCCAGGGC ACCCTGGTGA CAGTGTCTTC
CGCTAGCACC AAGGGCCCAA GCGTGTTTCC AGAGGCTCCA AGCTCTAAGT CCACCAGCGG AGGAACAGCC

| Amino Acid and Nucleotide Sequences |
|---|
| GCTCTGGGCT GTCTGGTGAC CGACTACTTC CCAGAGCCCG TGACAGTGTC CTGGAACAGC GGCGCTCTGA<br>CCTCTGGCGT GCACACATTT CCAGCCGTGC TGGAGTCCAG CGGCCTGTAC TCCCTGTGGT CCGTGGTGAC<br>CGTGCCCAGC TCTTCCCTGG GCACCCAGAC ATATATCTGC AACGTGAATC ACAAGCCATC CAATACAAAG<br>GTGGACAAGA GGGTGGAGCC CAAGAGCTGT GATAAGACCC ATACATGCCC CCCTTGTCCT GCTCCAGAGG<br>CTGCTGGAGG ACCATCCGTG TTCCTGTTTC CACCCAAGCC TAAGGACACC CTGATGATCA GCAGGACCCC<br>AGAGGTGACA TGCGTGGTGG TGTCCGTGTC CCACGAGGAC CCTGAGGTGA AGTTCAACTG GTACGTGGAT<br>GGCGTGGAGG TGCATAATGC TAAGACAAAG CCCAGGGAGG AGCAGTACAA CAGCACCTAT CGGGTGGTGT<br>CTGTGCTGAC AGTGCTGCAT CAGGATTGGC TGAACGGCAA GGAGTATAAG TGCAAGGTGT CTAATAAGGC<br>TCTGCCCGCC CCTATCGAGA GACCATCTC CAAGGCCAAG GGCCAGCCTA GAGAGCCACA GGTGTACGTG<br>TATCCTCCAA GCCGCGACGA GCTGACCAAG AACCAGGTGT CTCTGACATG TCTGGTGAAG GGCTTTTACC<br>CTTCTGATAT CGCTGTGGAG TGGGAGTCCA ATGGCCAGCC AGAGAACAAT TATAAGACCA CACCCCCTGT<br>GCTGGACTCT GATGGCTCCT TCGCCCTGGT GTCCAAGCTG ACCGTGGATA AGAGCAGGTG GCAGCAGGGC<br>AACGTGTTCT CCTGTTCTGT GATGCACGAG GCACTGCACA ACCATTACAC CCAGAAGTCC CTGTCCCTGA<br>GCCCCGGCAA A |

---

We claim:

1. An antibody that binds human PD-L1 comprising the amino acid sequence of SEQ ID NO: 1 and human TIM-3 comprising the amino acid sequence of SEQ ID NO: 2, the antibody comprising:
   a) a first heavy chain (HC) comprising the amino acid sequences of SEQ ID NO: 3, SEQ ID NO: 19, and SEQ ID NO: 22,
   b) a first light chain (LC) comprising the amino acid sequences of SEQ ID NO: 4 and SEQ ID NO: 27,
   c) a second HC comprising the amino acid sequences of SEQ ID NO: 5, SEQ ID NO: 23, and SEQ ID NO: 26,
   d) a second LC comprising the amino acid sequences of SEQ ID NO: 8 and SEQ ID NO: 28;
   and wherein, the first LC forms an inter-chain disulfide bond with the first HC, the second LC forms an inter-chain disulfide bond with the second HC, and the first HC forms two inter-chain disulfide bonds with the second HC, and the first HC and second HC are human IgG1 isotype.

2. An antibody that binds human PD-L1 comprising the amino acid sequence of SEQ ID NO: 1 and human TIM-3 comprising the amino acid sequence of SEQ ID NO: 2, the antibody comprising:
   e) a first heavy chain (HC) comprising the amino acid sequences of SEQ ID NO: 3, SEQ ID NO: 19, and SEQ ID NO: 22,
   f) a first light chain (LC) comprising the amino acid sequences of SEQ ID NO: 4 and SEQ ID NO: 27,
   g) a second HC comprising the amino acid sequences of SEQ ID NO: 6, SEQ ID NO: 23, and SEQ ID NO: 26,
   h) a second LC comprising the amino acid sequences of SEQ ID NO: 9 and SEQ ID NO: 28;
   and wherein, the first LC forms an inter-chain disulfide bond with the first HC, the second LC forms an inter-chain disulfide bond with the second HC, and the first HC forms two inter-chain disulfide bonds with the second HC, and the first HC and second HC are human IgG1 isotype.

3. The antibody of claim 1 or claim 2, wherein:
   a) the first HC comprises the amino acid sequences of SEQ ID NO: 20 and SEQ ID NO: 21, and
   b) the second HC comprises the amino acid sequences of SEQ ID NO: 24 and SEQ ID NO: 25.

4. A method of treating cancer, comprising administering to a patient in need thereof, an effective amount of the antibody of claim 3.

5. The method of claim 4, wherein the cancer is melanoma, lung cancer, head and neck cancer, liver cancer, colorectal cancer, pancreatic cancer, gastric cancer, kidney cancer, bladder cancer, prostate cancer, breast cancer, ovarian cancer, endometrial cancer, esophageal cancer, soft tissue sarcoma, cholangiocarcinoma, or hepatocellular carcinoma.

6. The method of claim 5, wherein the lung cancer is non-small cell lung cancer, small cell lung cancer, or mesothelioma.

7. The method of claim 4, further comprising administering simultaneously, separately, or sequentially one or more standard of care agents selected from the group consisting of cisplatin, carboplatin, dacarbazine, liposomal doxorubicin, docetaxel, cyclophosphamide and doxorubicin, navelbine, eribulin, paclitaxel, paclitaxel protein-bound particles for injectable suspension, ixabepilone, capecitabine, FOLFOX (leucovorin, fluorouracil, and oxaliplatin), FOLFIRI (leucovorin, fluorouracil, and irinotecan), gemcitabine, topotecan, liposomal irinotecan, pemetrexed, and cetuximab.

* * * * *

SEQUENCE LISTING

<160> NUMBER OF SEQ ID NOS: 32

<210> SEQ ID NO 1
<211> LENGTH: 290
<212> TYPE: PRT
<213> ORGANISM: Homo sapiens

<400> SEQUENCE: 1

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

```
Phe Ile Phe Arg Leu Arg Lys Gly Arg Met Met Asp Val Lys Lys Cys
                260                 265                 270

Gly Ile Gln Asp Thr Asn Ser Lys Gln Ser Asp Thr His Leu Glu
            275                 280                 285

Glu Thr
    290

<210> SEQ ID NO 2
<211> LENGTH: 130
<212> TYPE: PRT
<213> ORGANISM: Homo sapiens

<400> SEQUENCE: 2

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
            35                  40                  45

Val Pro Val Cys Trp Gly Lys Gly Ala Cys Pro Val Phe Glu Cys Gly
50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
            115                 120                 125

Ile Lys
    130

<210> SEQ ID NO 3
<211> LENGTH: 123
<212> TYPE: PRT
<213> ORGANISM: Artificial Sequence
<220> FEATURE:
<223> OTHER INFORMATION: synthetic construct

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Pro Asp Tyr Ser Pro Tyr Tyr Tyr Gly Met Asp Val
            100                 105                 110

Trp Gly Gln Gly Thr Thr Val Thr Val Ser Ser
            115                 120
```

<210> SEQ ID NO 4
<211> LENGTH: 111
<212> TYPE: PRT
<213> ORGANISM: Artificial Sequence
<220> FEATURE:
<223> OTHER INFORMATION: synthetic construct

<400> SEQUENCE: 4

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Gln Ser Tyr Asp Ser Ser Leu
                85                  90                  95

Ser Gly Ser Val Phe Gly Gly Gly Ile Lys Leu Thr Val Leu Gly
            100                 105                 110
```

<210> SEQ ID NO 5
<211> LENGTH: 117
<212> TYPE: PRT
<213> ORGANISM: Artificial Sequence
<220> FEATURE:
<223> OTHER INFORMATION: synthetic construct

<400> SEQUENCE: 5

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ala Arg Thr Ala Phe Asp Leu Trp Gly Gln Gly Thr Leu
            100                 105                 110

Val Thr Val Ser Ser
        115
```

<210> SEQ ID NO 6
<211> LENGTH: 117
<212> TYPE: PRT
<213> ORGANISM: Artificial Sequence
<220> FEATURE:
<223> OTHER INFORMATION: synthetic construct

<400> SEQUENCE: 6

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Phe
```

```
            20                  25                  30
Tyr Phe Ser Trp Val Arg Gln Ala Pro Gly Lys Gly Leu Glu Trp Val
        35                  40                  45

Ser Ala Ile Ser Gly Asn Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Asn Thr Gly Phe Asp Leu Trp Gly Gln Gly Thr Leu
            100                 105                 110

Val Thr Val Ser Ser
        115

<210> SEQ ID NO 7
<211> LENGTH: 117
<212> TYPE: PRT
<213> ORGANISM: Artificial Sequence
<220> FEATURE:
<223> OTHER INFORMATION: synthetic construct

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Ala Ile Ser Gly Asn Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Asn Thr Gly Phe Asp Leu Trp Gly Gln Gly Thr Leu
            100                 105                 110

Val Thr Val Ser Ser
        115

<210> SEQ ID NO 8
<211> LENGTH: 107
<212> TYPE: PRT
<213> ORGANISM: Artificial Sequence
<220> FEATURE:
<223> OTHER INFORMATION: synthetic construct

<400> SEQUENCE: 8

Asp Ile Val Met Thr Gln Ser Pro Ser Ser Leu Ser Ala Ser Val Gly
1               5                   10                  15

Asp Arg Val Thr Ile Thr Cys Gln Ala Ser Glu Ala Ile Tyr Gly Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Pro Ile Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Ala Tyr Gly Phe Pro Pro
            85                  90                  95

Thr Phe Gly Gln Gly Thr Lys Leu Glu Ile Lys
        100                 105

<210> SEQ ID NO 9
<211> LENGTH: 107
<212> TYPE: PRT
<213> ORGANISM: Artificial Sequence
<220> FEATURE:
<223> OTHER INFORMATION: synthetic construct

<400> SEQUENCE: 9

Asp Ile Val Met Thr Gln Ser Pro Ser Ser Leu Ser Ala Ser Val Gly
1               5                   10                  15

Asp Arg Val Thr Ile Thr Cys Gln Ala Ser Glu Ala Ile Tyr Gly Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Pro Ile Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Gly Phe Pro Pro
            85                  90                  95

Thr Phe Gly Gln Gly Thr Lys Leu Glu Ile Lys
        100                 105

<210> SEQ ID NO 10
<211> LENGTH: 107
<212> TYPE: PRT
<213> ORGANISM: Artificial Sequence
<220> FEATURE:
<223> OTHER INFORMATION: synthetic construct

<400> SEQUENCE: 10

Asp Ile Val Met Thr Gln Ser Pro Ser Ser Leu Ser Ala Ser Val Gly
1               5                   10                  15

Asp Gly Val Thr Ile Thr Cys Gln Ala Ser Gln Asp Ile Tyr Asn Tyr
            20                  25                  30

Leu Asn Trp Tyr Gln Gln Lys Pro Gly Lys Ala Pro Lys Leu Leu Ile
        35                  40                  45

Tyr Tyr Ala Ser Ser Ile Val Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ser Ser Phe Pro Pro
            85                  90                  95

Thr Phe Gly Gln Gly Thr Lys Leu Glu Ile Lys
        100                 105

<210> SEQ ID NO 11
<211> LENGTH: 453
<212> TYPE: PRT
<213> ORGANISM: Artificial Sequence
<220> FEATURE:
<223> OTHER INFORMATION: synthetic construct

<400> SEQUENCE: 11

Gln Val Gln Leu Val Gln Ser Gly Ala Glu Val Lys Lys Pro Gly Ser

```
  1               5                  10                 15
Ser Val Lys Val Ser Cys Lys Ala Ser Gly Gly Thr Phe Ser Ser Tyr
             20                 25                 30

Ala Ile Ser Trp Val Arg Gln Ala Pro Gly Gln Gly Leu Glu Trp Met
             35                 40                 45

Gly Gly Ile Ile Pro Ile Phe Gly Thr Ala Asn Tyr Ala Gln Lys Phe
             50                 55                 60

Gln Gly Arg Val Thr Ile Thr Ala Asp Lys Ser Thr Ser Thr Ala Tyr
 65                 70                 75                 80

Met Glu Leu Ser Ser Leu Arg Ser Glu Asp Thr Ala Val Tyr Tyr Cys
                 85                 90                 95

Ala Arg Ser Pro Asp Tyr Ser Pro Tyr Tyr Tyr Gly Met Asp Val
                100                105                110

Trp Gly Gln Gly Thr Thr Val Thr Val Ser Ser Ala Ser Thr Lys Gly
                115                120                125

Pro Ser Val Phe Pro Leu Ala Pro Ser Ser Lys Ser Thr Ser Gly Gly
                130                135                140

Thr Ala Ala Leu Gly Cys Leu Val Lys Asp Tyr Phe Pro Glu Pro Val
145                150                155                160

Thr Val Ser Trp Asn Ser Gly Ala Leu Thr Ser Gly Val His Thr Phe
                165                170                175

Pro Ala Val Leu Gln Ser Ser Gly Leu Tyr Ser Leu Ser Ser Val Val
                180                185                190

Thr Val Pro Ser Ser Ser Leu Gly Thr Gln Thr Tyr Ile Cys Asn Val
                195                200                205

Asn His Lys Pro Ser Asn Thr Lys Val Asp Lys Arg Val Glu Pro Lys
210                215                220

Ser Cys Asp Lys Thr His Thr Cys Pro Pro Cys Pro Ala Pro Glu Ala
225                230                235                240

Ala Gly Gly Pro Ser Val Phe Leu Phe Pro Pro Lys Pro Lys Asp Thr
                245                250                255

Leu Met Ile Ser Arg Thr Pro Glu Val Thr Cys Val Val Val Ser Val
                260                265                270

Ser His Glu Asp Pro Glu Val Lys Phe Asn Trp Tyr Val Asp Gly Val
                275                280                285

Glu Val His Asn Ala Lys Thr Lys Pro Arg Glu Glu Gln Tyr Asn Ser
                290                295                300

Thr Tyr Arg Val Val Ser Val Leu Thr Val Leu His Gln Asp Trp Leu
305                310                315                320

Asn Gly Lys Glu Tyr Lys Cys Lys Val Ser Asn Lys Ala Leu Pro Ala
                325                330                335

Pro Ile Glu Lys Thr Ile Ser Lys Ala Lys Gly Gln Pro Arg Glu Pro
                340                345                350

Gln Val Tyr Val Leu Pro Pro Ser Arg Asp Glu Leu Thr Lys Asn Gln
                355                360                365

Val Ser Leu Leu Cys Leu Val Lys Gly Phe Tyr Pro Ser Asp Ile Ala
                370                375                380

Val Glu Trp Glu Ser Asn Gly Gln Pro Glu Asn Asn Tyr Leu Thr Trp
385                390                395                400

Pro Pro Val Leu Asp Ser Asp Gly Ser Phe Phe Leu Tyr Ser Lys Leu
                405                410                415

Thr Val Asp Lys Ser Arg Trp Gln Gln Gly Asn Val Phe Ser Cys Ser
                420                425                430
```

Val Met His Glu Ala Leu His Asn His Tyr Thr Gln Lys Ser Leu Ser
        435                 440                 445

Leu Ser Pro Gly Lys
    450

<210> SEQ ID NO 12
<211> LENGTH: 216
<212> TYPE: PRT
<213> ORGANISM: Artificial Sequence
<220> FEATURE:
<223> OTHER INFORMATION: synthetic construct

<400> SEQUENCE: 12

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Gln Ser Tyr Asp Ser Ser Leu
                85                  90                  95

Ser Gly Ser Val Phe Gly Gly Gly Ile Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Glu Ser Glu Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Ala Glu Cys Ser
    210                 215

<210> SEQ ID NO 13
<211> LENGTH: 447
<212> TYPE: PRT
<213> ORGANISM: Artificial Sequence
<220> FEATURE:
<223> OTHER INFORMATION: synthetic construct

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val

```
            50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Ala Arg Thr Ala Phe Asp Leu Trp Gly Gln Gly Thr Leu
            100                 105                 110

Val Thr Val Ser Ser Ala Ser Thr Lys Gly Pro Ser Val Phe Pro Glu
            115                 120                 125

Ala Pro Ser Ser Lys Ser Thr Ser Gly Gly Thr Ala Ala Leu Gly Cys
            130                 135                 140

Leu Val Thr Asp Tyr Phe Pro Glu Pro Val Thr Val Ser Trp Asn Ser
145                 150                 155                 160

Gly Ala Leu Thr Ser Gly Val His Thr Phe Pro Ala Val Leu Glu Ser
                165                 170                 175

Ser Gly Leu Tyr Ser Leu Trp Ser Val Val Thr Val Pro Ser Ser Ser
                180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys Asp Lys Thr His
            210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Ser Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Val Tyr Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Ala Leu Val Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 14
<211> LENGTH: 447
<212> TYPE: PRT
<213> ORGANISM: Artificial Sequence
```

<220> FEATURE:
<223> OTHER INFORMATION: synthetic construct

<400> SEQUENCE: 14

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Phe
            20                  25                  30

Tyr Phe Ser Trp Val Arg Gln Ala Pro Gly Lys Gly Leu Glu Trp Val
        35                  40                  45

Ser Ala Ile Ser Gly Asn Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Asn Thr Gly Phe Asp Leu Trp Gly Gln Gly Thr Leu
            100                 105                 110

Val Thr Val Ser Ser Ala Ser Thr Lys Gly Pro Ser Val Phe Pro Glu
        115                 120                 125

Ala Pro Ser Ser Lys Ser Thr Ser Gly Gly Thr Ala Ala Leu Gly Cys
    130                 135                 140

Leu Val Thr Asp Tyr Phe Pro Glu Pro Val Thr Val Ser Trp Asn Ser
145                 150                 155                 160

Gly Ala Leu Thr Ser Gly Val His Thr Phe Pro Ala Val Leu Glu Ser
                165                 170                 175

Ser Gly Leu Tyr Ser Leu Trp Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Ser Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Val Tyr Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400
```

Asp Gly Ser Phe Ala Leu Val Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 15
<211> LENGTH: 447
<212> TYPE: PRT
<213> ORGANISM: Artificial Sequence
<220> FEATURE:
<223> OTHER INFORMATION: synthetic construct

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
            35                  40                  45

Ser Ala Ile Ser Gly Asn Gly Lys Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Asn Thr Gly Phe Asp Leu Trp Gly Gln Gly Thr Leu
            100                 105                 110

Val Thr Val Ser Ser Ala Ser Thr Lys Gly Pro Ser Val Phe Pro Glu
        115                 120                 125

Ala Pro Ser Ser Lys Ser Thr Ser Gly Gly Thr Ala Ala Leu Gly Cys
    130                 135                 140

Leu Val Thr Asp Tyr Phe Pro Glu Pro Val Thr Val Ser Trp Asn Ser
145                 150                 155                 160

Gly Ala Leu Thr Ser Gly Val His Thr Phe Pro Ala Val Leu Glu Ser
                165                 170                 175

Ser Gly Leu Tyr Ser Leu Trp Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Ser Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Val Tyr Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Ala Leu Val Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 16
<211> LENGTH: 214
<212> TYPE: PRT
<213> ORGANISM: Artificial Sequence
<220> FEATURE:
<223> OTHER INFORMATION: synthetic construct

<400> SEQUENCE: 16

Asp Ile Val Met Thr Gln Ser Pro Ser Ser Leu Ser Ala Ser Val Gly
1               5                   10                  15

Asp Gly Val Thr Ile Thr Cys Gln Ala Ser Gln Asp Ile Tyr Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Pro
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Arg Val Gly Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Arg
                165                 170                 175

Ser Ala Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 17

```
<211> LENGTH: 214
<212> TYPE: PRT
<213> ORGANISM: Artificial Sequence
<220> FEATURE:
<223> OTHER INFORMATION: synthetic construct

<400> SEQUENCE: 17

Asp Ile Val Met Thr Gln Ser Pro Ser Ser Leu Ser Ala Ser Val Gly
1               5                   10                  15

Asp Arg Val Thr Ile Thr Cys Gln Ala Ser Glu Ala Ile Tyr Gly Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Pro Ile Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Gly Phe Pro Pro
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Arg Val Gly Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Arg
                165                 170                 175

Ser Ala Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 18
<211> LENGTH: 214
<212> TYPE: PRT
<213> ORGANISM: Artificial Sequence
<220> FEATURE:
<223> OTHER INFORMATION: synthetic construct

<400> SEQUENCE: 18

Asp Ile Val Met Thr Gln Ser Pro Ser Ser Leu Ser Ala Ser Val Gly
1               5                   10                  15

Asp Gly Val Thr Ile Thr Cys Gln Ala Ser Gln Asp Ile Tyr Asn Tyr
            20                  25                  30

Leu Asn Trp Tyr Gln Gln Lys Pro Gly Lys Ala Pro Lys Leu Leu Ile
        35                  40                  45

Tyr Tyr Ala Ser Ser Ile Val Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ser Ser Phe Pro Pro
                85                  90                  95

Thr Phe Gly Gln Gly Thr Lys Leu Glu Ile Lys Arg Thr Val Ala Ala
```

```
                100             105                 110
Pro Ser Val Phe Ile Phe Pro Ser Asp Glu Gln Leu Lys Ser Gly
        115                 120             125

Thr Ala Arg Val Gly Cys Leu Leu Asn Asn Phe Tyr Pro Arg Glu Ala
        130                 135             140

Lys Val Gln Trp Lys Val Asp Asn Ala Leu Gln Ser Gly Asn Ser Gln
145                 150             155                 160

Glu Ser Val Thr Glu Gln Asp Ser Lys Asp Ser Thr Tyr Ser Leu Arg
                165             170                 175

Ser Ala Leu Thr Leu Ser Lys Ala Asp Tyr Glu Lys His Lys Val Tyr
        180                 185             190

Ala Cys Glu Val Thr His Gln Gly Leu Ser Ser Pro Val Thr Lys Ser
        195                 200             205

Phe Asn Arg Gly Glu Cys
    210

<210> SEQ ID NO 19
<211> LENGTH: 63
<212> TYPE: PRT
<213> ORGANISM: Artificial Sequence
<220> FEATURE:
<223> OTHER INFORMATION: synthetic construct

<400> SEQUENCE: 19

Gly Pro Ser Val Phe Pro Leu Ala Pro Ser Ser Lys Ser Thr Ser Gly
1               5                   10                  15

Gly Thr Ala Ala Leu Gly Cys Leu Val Lys Asp Tyr Phe Pro Glu Pro
            20                  25                  30

Val Thr Val Ser Trp Asn Ser Gly Ala Leu Thr Ser Gly Val His Thr
        35                  40                  45

Phe Pro Ala Val Leu Gln Ser Ser Gly Leu Tyr Ser Leu Lys Ser
    50                  55                  60

<210> SEQ ID NO 20
<211> LENGTH: 35
<212> TYPE: PRT
<213> ORGANISM: Artificial Sequence
<220> FEATURE:
<223> OTHER INFORMATION: synthetic construct

<400> SEQUENCE: 20

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Ser
        35

<210> SEQ ID NO 21
<211> LENGTH: 11
<212> TYPE: PRT
<213> ORGANISM: Artificial Sequence
<220> FEATURE:
<223> OTHER INFORMATION: synthetic construct

<400> SEQUENCE: 21

Ser Asn Lys Ala Leu Pro Ala Pro Ile Glu Lys
1               5                   10

<210> SEQ ID NO 22
```

<211> LENGTH: 61
<212> TYPE: PRT
<213> ORGANISM: Artificial Sequence
<220> FEATURE:
<223> OTHER INFORMATION: synthetic construct

<400> SEQUENCE: 22

Arg Glu Pro Gln Val Tyr Val Leu Pro Pro Ser Arg Asp Glu Leu Thr
1               5                   10                  15

Lys Asn Gln Val Ser Leu Leu Cys Leu Val Lys Gly Phe Tyr Pro Ser
            20                  25                  30

Asp Ile Ala Val Glu Trp Glu Ser Asn Gly Gln Pro Glu Asn Asn Tyr
        35                  40                  45

Leu Thr Trp Pro Pro Val Leu Asp Ser Asp Gly Ser Phe
    50                  55                  60

<210> SEQ ID NO 23
<211> LENGTH: 63
<212> TYPE: PRT
<213> ORGANISM: Artificial Sequence
<220> FEATURE:
<223> OTHER INFORMATION: synthetic construct

<400> SEQUENCE: 23

Glu Ala Pro Ser Ser Lys Ser Thr Ser Gly Gly Thr Ala Ala Leu Gly
1               5                   10                  15

Cys Leu Val Thr Asp Tyr Phe Pro Glu Pro Val Thr Val Ser Trp Asn
            20                  25                  30

Ser Gly Ala Leu Thr Ser Gly Val His Thr Phe Pro Ala Val Leu Glu
        35                  40                  45

Ser Ser Gly Leu Tyr Ser Leu Trp Ser Val Val Thr Val Pro Ser
    50                  55                  60

<210> SEQ ID NO 24
<211> LENGTH: 35
<212> TYPE: PRT
<213> ORGANISM: Artificial Sequence
<220> FEATURE:
<223> OTHER INFORMATION: synthetic construct

<400> SEQUENCE: 24

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Ser
        35

<210> SEQ ID NO 25
<211> LENGTH: 11
<212> TYPE: PRT
<213> ORGANISM: Artificial Sequence
<220> FEATURE:
<223> OTHER INFORMATION: synthetic construct

<400> SEQUENCE: 25

Ala Pro Ile Glu Lys Thr Ile Ser Lys Ala Lys
1               5                   10

<210> SEQ ID NO 26
<211> LENGTH: 61
<212> TYPE: PRT
<213> ORGANISM: Artificial Sequence
<220> FEATURE:
<223> OTHER INFORMATION: synthetic construct

<400> SEQUENCE: 26

Val Tyr Pro Pro Ser Arg Asp Glu Leu Thr Lys Asn Gln Val Ser Leu
1               5                   10                  15

Thr Cys Leu Val Lys Gly Phe Tyr Pro Ser Asp Ile Ala Val Glu Trp
            20                  25                  30

Glu Ser Asn Gly Gln Pro Glu Asn Asn Tyr Lys Thr Thr Pro Pro Val
        35                  40                  45

Leu Asp Ser Asp Gly Ser Phe Ala Leu Val Ser Lys Leu
    50                  55                  60

<210> SEQ ID NO 27
<211> LENGTH: 51
<212> TYPE: PRT
<213> ORGANISM: Artificial Sequence
<220> FEATURE:
<223> OTHER INFORMATION: synthetic construct

<400> SEQUENCE: 27

Ala Asn Lys Ala Thr Leu Val Cys Leu Ile Ser Asp Phe Tyr Pro Gly
1               5                   10                  15

Ala Val Thr Val Ala Trp Lys Ala Asp Ser Ser Pro Val Lys Ala Gly
            20                  25                  30

Val Glu Thr Thr Thr Pro Ser Lys Gln Ser Asn Asn Lys Tyr Ala Ala
        35                  40                  45

Glu Ser Glu
    50

<210> SEQ ID NO 28
<211> LENGTH: 51
<212> TYPE: PRT
<213> ORGANISM: Artificial Sequence
<220> FEATURE:
<223> OTHER INFORMATION: synthetic construct

<400> SEQUENCE: 28

Arg Val Gly Cys Leu Leu Asn Asn Phe Tyr Pro Arg Glu Ala Lys Val
1               5                   10                  15

Gln Trp Lys Val Asp Asn Ala Leu Gln Ser Gly Asn Ser Gln Glu Ser
            20                  25                  30

Val Thr Glu Gln Asp Ser Lys Asp Ser Thr Tyr Ser Leu Arg Ser Ala
        35                  40                  45

Leu Thr Leu
    50

<210> SEQ ID NO 29
<211> LENGTH: 787
<212> TYPE: DNA
<213> ORGANISM: Artificial Sequence
<220> FEATURE:
<223> OTHER INFORMATION: synthetic construct

<400> SEQUENCE: 29
cagtccgtcc tgactcagcc accttccgct agcggtaccc ccggccagag agtgacaatc      60
tcatgctccg gttccagctc taacattggc tctaacactg tcaattggta ccagcagctg     120
ccaggaaccg caccaaagct gctgatctat ggaaactcaa ataggcctag cggggtgcca     180
gaccggttta gcggatctaa aagtgggact tcagcttccc tggcaatttc tggactgcag     240

| | |
|---|---|
| agtgaggacg aagctgatta ctattgccag tcctacgata gttcactgag cggttccgtg | 300 |
| ttcggcggag ggatcaagct gacagtcctg ggccagccca aggtgagttc tagaggatcc | 360 |
| atctgggata agcatgctgt tttctgtctg tccctaacat gccctgtgat tatccgcaaa | 420 |
| caacacaccc aagggcagaa cttttgttact taaacaccat cctgtttgct tctttcctca | 480 |
| ggccgctcct tccgtgactc tgtttccccc ttccagcgag gaactgcagg ccaataaggc | 540 |
| caccctggtg tgcctgatta gcgacttcta tcctggagct gtgacagtcg catggaaggc | 600 |
| cgattctagt ccagtgaaag caggggtcga gaccacaact ccctccaagc agagcaacaa | 660 |
| caagtacgca gccgagtctg aactgagtct gaccccagaa cagtggaagt cccacaggag | 720 |
| ttattcatgc caggtgaccc atgagggctc cacagtggag aagaccgtgg cccctgctga | 780 |
| gtgtagc | 787 |

<210> SEQ ID NO 30
<211> LENGTH: 642
<212> TYPE: DNA
<213> ORGANISM: Artificial Sequence
<220> FEATURE:
<223> OTHER INFORMATION: synthetic construct

<400> SEQUENCE: 30

| | |
|---|---|
| gacatcgtga tgacccagtc cccttccagc ctgtctgcct ccgtgggcga cggagtgacc | 60 |
| atcacatgcc aggctagcca ggatatctac aactatctga attggtacca gcagaagcct | 120 |
| ggcaaggccc caaagctgct gatctattac gcttcttcca tcgtgtctgg agtgccatcc | 180 |
| aggttcagcg gatctggatc cggaaccgac tttaccctga caatcagctc tctgcagcct | 240 |
| gaggatttcg ccacatacta ttgccagcag gcttcctctt ccccccctac ctttggccag | 300 |
| ggcacaaagc tggagatcaa gagaaccgtg gccgctccat ccgtgttcat cttttccaccc | 360 |
| agcgacgagc agctgaagtc tggcacagct agggtgggct gtctgctgaa caacttctac | 420 |
| ccccgggagg ccaaggtgca gtggaaggtg gataacgctc tgcagagcgg caattctcag | 480 |
| gagtccgtga ccgagcagga cagcaaggat tctacatatt ccctgagaag cgccctgaca | 540 |
| ctgagcaagg ccgattacga aagcacaag gtgtatgctt gcgaggtgac ccatcagggc | 600 |
| ctgtccagcc cagtgacaaa gtctttcaat cgcggcgagt gt | 642 |

<210> SEQ ID NO 31
<211> LENGTH: 1359
<212> TYPE: DNA
<213> ORGANISM: Artificial Sequence
<220> FEATURE:
<223> OTHER INFORMATION: synthetic construct

<400> SEQUENCE: 31

| | |
|---|---|
| caggtccagc tggtgcagag cggagccgaa gtgaagaaac ccggtagcag cgtcaaagtg | 60 |
| tcatgtaaag cctcagggggg aacattctcc agctacgcca tctcctgggt gagacaggct | 120 |
| ccaggacagg gactggagtg gatgggagga atcatcccta tcttcggcac cgccaactac | 180 |
| gctcagaagt ttcagggccg cgtgaccatc acagccgaca agagcacctc tacagcttat | 240 |
| atggagctgt cttccctgag aagcgaggat acagccgtgt actattgcgc tgctcccccc | 300 |
| gactacagcc ttactatta ctatggcatg gacgtgtggg gccagggcac cacagtgacc | 360 |
| gtgagctctg ctagcacaaa gggcccatcc gtgttcccac tggctccatc cagcaagtcc | 420 |
| accagcggag gaacagccgc tctgggctgt ctggtgaagg actatttccc agagccagtg | 480 |
| accgtgtcct ggaacagcgg cgccctgacc tctggagtgc acacatttcc cgctgtgctg | 540 |

```
cagtcttccg gcctgtactc tctgaagtcc gtggtgaccg tgcctagctc ttccctgggc      600
acccagacat atatctgcaa cgtgaatcac aagccttcca atacaaaggt ggacaagagg      660
gtggagccaa agagctgtga taagacccat acatgccccc cttgtcctgc tccagaggct      720
gctggaggac caagcgtgtt cctgtttcca cccaagccca aggacaccct gatgatctct      780
aggacccctg aggtgacatg cgtggtggtg tccgtgtccc acgaggaccc agaggtgaag      840
tttaactggt acgtggatgg cgtggaggtg cataatgcta agaccaagcc tagggaggag      900
cagtacaaca gcacctatcg ggtggtgtct gtgctgacag tgctgcatca ggattggctg      960
aacggcaagg agtataagtg caaggtgtct aataaggccc tgcccgctcc tatcgagaag     1020
accatctcca aggccaaggg ccagcctagg gagccacagg tgtacgtgct gcctccaagc     1080
cgggacgagc tgacaaagaa ccaggtgtct ctgctgtgcc tggtgaaggg cttctatcca     1140
tctgatatcg ctgtggagtg ggagtccaat ggccagcccg agaacaatta cctgacctgg     1200 cccccgtgc tggacagcga tggctctttc tttctgtatt ccaagctgac agtggataag     1260
agccggtggc agcagggcaa cgtgttctcc tgttctgtga tgcacgaggc actgcacaat     1320
cattacaccc agaaatccct gtcactgagc cccggcaag                            1359
```

<210> SEQ ID NO 32
<211> LENGTH: 1341
<212> TYPE: DNA
<213> ORGANISM: Artificial Sequence
<220> FEATURE:
<223> OTHER INFORMATION: synthetic construct

<400> SEQUENCE: 32

```
gaggtgcagc tgctggagtc tggggggggt ctggtgcagc cgggggtag cctgcgtctg       60 tcttgtgccg cctctgggtt tacttttcc agctactata tgagctgggt gagacaggct      120
cctggcaagg gcctggagtg ggtgtctgcc atcagcggca acggcaaatc tacctactat      180
gctgactccg tgaagggcag attcaccatc agccgcgata actctaagaa tacactgtac      240
ctgcagatga acagcctgcg cgctgaggac accgccgtgt actattgcgc cagatattat      300
aacacaggct tcgatctgtg gggccagggc accctgtga cagtgtcttc cgctagcacc       360
aagggcccaa gcgtgtttcc agaggctcca agctctaagt ccaccagcgg aggaacagcc      420
gctctgggct gtctggtgac cgactacttc ccagagcccg tgacagtgtc ctggaacagc      480
ggcgctctga cctctggcgt gcacacattt ccagccgtgc tggagtccag cggcctgtac      540
tccctgtggt ccgtggtgac cgtgcccagc tcttccctgg gcacccagac atatatctgc      600
aacgtgaatc acaagccatc caatacaaag gtggacaaga gggtggagcc caagagctgt      660
gataagaccc atacatgccc ccttgtcct gctccagagg ctgctggagg accatccgtg      720
ttcctgtttc cacccaagcc taaggacacc ctgatgatca gcaggacccc agaggtgaca      780
tgcgtggtgg tgtccgtgtc ccacgaggac cctgaggtga agttcaactg gtacgtggat      840
ggcgtggagg tgcataatgc taagacaaag cccagggagg agcagtacaa cagcacctat      900
cgggtggtgt ctgtgctgac agtgctgcat caggattggc tgaacggcaa ggagtataag      960
tgcaaggtgt ctaataaggc tctgcccgcc cctatcgaga gaccatctc caaggccaag     1020 ggccagccta gagagccaca ggtgtacgtg tatcctccaa gccgcgacga gctgaccaag     1080
aaccaggtgt ctctgacatg tctggtgaag ggcttttacc cttctgatat cgctgtggag     1140
tgggagtcca atggccagcc agagaacaat tataagacca cccccctgt gctggactct     1200
```

```
gatggctcct tcgccctggt gtccaagctg accgtggata agagcaggtg gcagcagggc    1260
aacgtgttct cctgttctgt gatgcacgag gcactgcaca accattacac ccagaagtcc    1320
ctgtccctga gccccggcaa a                                              1341
```